US010125123B2

(12) United States Patent
Glimcher et al.

(10) Patent No.: US 10,125,123 B2
(45) Date of Patent: Nov. 13, 2018

(54) SMALL MOLECULE IRE1-α INHIBITORS

(71) Applicant: Cornell University, Ithaca, NY (US)

(72) Inventors: Laurie H. Glimcher, New York, NY (US); Sarah Elizabeth Bettigole, New York, NY (US); Juan Rodrigo Cubillos Ruiz, New York, NY (US); Joseph P. Vacca, Telford, PA (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/449,547

(22) Filed: Mar. 3, 2017

(65) Prior Publication Data
US 2017/0253590 A1 Sep. 7, 2017

Related U.S. Application Data

(60) Provisional application No. 62/303,236, filed on Mar. 3, 2016, provisional application No. 62/303,951, filed on Mar. 4, 2016.

(51) Int. Cl.
| C07D 403/14 | (2006.01) |
| C07D 401/04 | (2006.01) |
| C07D 403/04 | (2006.01) |
| C07D 401/14 | (2006.01) |
| C07D 407/14 | (2006.01) |
| C07D 413/04 | (2006.01) |
| C07D 413/14 | (2006.01) |
| C07D 471/04 | (2006.01) |
| A61K 31/429 | (2006.01) |
| A61K 31/496 | (2006.01) |
| A61K 31/497 | (2006.01) |
| A61K 31/4985 | (2006.01) |
| A61K 31/5025 | (2006.01) |
| A61K 31/506 | (2006.01) |
| A61K 31/5377 | (2006.01) |
| A61K 31/541 | (2006.01) |
| A61K 31/542 | (2006.01) |
| A61K 31/4155 | (2006.01) |
| A61K 31/4162 | (2006.01) |
| A61K 31/4188 | (2006.01) |
| A61K 31/423 | (2006.01) |
| A61K 31/437 | (2006.01) |
| A61K 31/4406 | (2006.01) |
| A61K 31/4439 | (2006.01) |
| A61K 31/444 | (2006.01) |
| A61K 31/4709 | (2006.01) |
| A61K 31/4725 | (2006.01) |
| A61K 31/498 | (2006.01) |
| A61K 31/517 | (2006.01) |
| A61K 31/519 | (2006.01) |

(Continued)

(52) U.S. Cl.
CPC ........ *C07D 403/14* (2013.01); *A61K 31/4155* (2013.01); *A61K 31/4162* (2013.01); *A61K 31/4188* (2013.01); *A61K 31/423* (2013.01); *A61K 31/429* (2013.01); *A61K 31/437* (2013.01); *A61K 31/444* (2013.01); *A61K 31/4406* (2013.01); *A61K 31/4439* (2013.01); *A61K 31/4709* (2013.01); *A61K 31/4725* (2013.01); *A61K 31/496* (2013.01); *A61K 31/497* (2013.01); *A61K 31/498* (2013.01); *A61K 31/4985* (2013.01); *A61K 31/506* (2013.01); *A61K 31/5025* (2013.01); *A61K 31/517* (2013.01); *A61K 31/519* (2013.01); *A61K 31/536* (2013.01); *A61K 31/5377* (2013.01); *A61K 31/541* (2013.01); *A61K 31/542* (2013.01); *A61K 31/55* (2013.01); *C07D 401/04* (2013.01); *C07D 401/10* (2013.01); *C07D 401/14* (2013.01); *C07D 403/04* (2013.01); *C07D 403/10* (2013.01); *C07D 407/14* (2013.01); *C07D 409/14* (2013.01); *C07D 413/04* (2013.01); *C07D 413/14* (2013.01); *C07D 471/04* (2013.01); *C07D 487/04* (2013.01)

(58) Field of Classification Search
CPC .. C07D 403/14; C07D 401/04; C07D 403/04; C07D 401/14
See application file for complete search history.

(56) References Cited

U.S. PATENT DOCUMENTS

| 5,554,630 | A | * | 9/1996 | Teuber | ................. | C07D 231/12 |
| | | | | | | 514/233.2 |
| 2002/0016326 | A1 | | 2/2002 | Galemmo et al. | | |

(Continued)

FOREIGN PATENT DOCUMENTS

| EP | 1724258 A1 | 11/2006 |
| EP | 1867648 A1 | 12/2007 |

(Continued)

OTHER PUBLICATIONS

National Center for Biotechnology Information. PubChem Compound Database; CID=11763847, https://pubchem.ncbi.nlm.nih.gov/compound/11763847 (created Oct. 26, 2006 accessed Oct. 30, 2017) (Year: 2006).*

(Continued)

*Primary Examiner* — Matthew P Coughlin
(74) *Attorney, Agent, or Firm* — Schwegman, Lundberg & Woessner, P.A.

(57) ABSTRACT

Described herein are IRE1α inhibitors, compositions containing such inhibitors, and methods of treatment that include administration of such compounds. Exemplary compounds are provided throughout the application.

14 Claims, 3 Drawing Sheets

Specification includes a Sequence Listing.

(51) Int. Cl.
  *A61K 31/536* (2006.01)
  *A61K 31/55* (2006.01)
  *C07D 401/10* (2006.01)
  *C07D 403/10* (2006.01)
  *C07D 409/14* (2006.01)
  *C07D 487/04* (2006.01)

(56) References Cited

U.S. PATENT DOCUMENTS

| | | | | |
|---|---|---|---|---|
| 2007/0278938 A1* | 12/2007 | Yabunouchi | ......... | C07D 307/91 313/504 |
| 2012/0130069 A1* | 5/2012 | Sim | ...................... | C07D 401/12 544/80 |
| 2017/0252350 A1 | 9/2017 | Glimcher et al. | | |

FOREIGN PATENT DOCUMENTS

| | | |
|---|---|---|
| EP | 2070929 A1 | 6/2009 |
| EP | 2277881 A1 | 1/2011 |
| EP | 2426135 A1 | 3/2012 |
| EP | 2532661 A1 | 12/2012 |
| EP | 2896620 A1 | 7/2015 |
| EP | 2927232 A1 | 10/2015 |
| WO | WO-9857951 A1 | 12/1998 |
| WO | WO-2004100946 A1 | 11/2004 |
| WO | WO-2005121147 A1 | 12/2005 |
| WO | WO-2006018662 A2 | 2/2006 |
| WO | WO-2006044823 A2 | 4/2006 |
| WO | WO-2006071940 A2 | 7/2006 |
| WO | WO-2007067836 A2 | 6/2007 |
| WO | WO-2007075869 A2 | 7/2007 |
| WO | WO-2007095588 A1 | 8/2007 |
| WO | WO-2008021388 A1 | 2/2008 |
| WO | WO-2008054702 A1 | 5/2008 |
| WO | WO-2009038385 A2 | 3/2009 |
| WO | WO-2009065096 A1 | 5/2009 |
| WO | WO-2009074260 A1 | 6/2009 |
| WO | WO-2011025706 A2 | 3/2011 |
| WO | WO-2011047384 A2 | 4/2011 |
| WO | WO-2013059587 A1 | 4/2013 |
| WO | WO-2014052669 A1 | 4/2014 |
| WO | WO-2014072220 A1 | 5/2014 |
| WO | WO -2014088284 A1 * | 6/2014  ........... C07D 209/82 |
| WO | WO-2015108490 A2 | 7/2015 |
| WO | WO-201715217 A1 | 9/2017 |
| WO | WO-2017152126 A1 | 9/2017 |
| WO | WO-2017152874 A1 | 9/2017 |

OTHER PUBLICATIONS

National Center for Biotechnology Information. PubChem Compound Database; CID=69457088, https://pubchem.ncbi.nlm.nih.gov/compound/69457088 (created Dec. 1, 2012; accessed Oct. 30, 2017). (Year: 2012).*

"U.S. Appl. No. 15/449,610, Response filed Sep. 28, 2017 to Restriction Requirement dated Aug. 15, 2017", 6 pgs.
"U.S. Appl. No. 15/449,610, Restriction Requirement dated Sep. 15, 2017", 6 pgs.
"International Application Serial No. PCT/US2017/020773, International Search Report dated May 23, 2017", 15 pgs.
"International Application Serial No. PCT/US2017/020773, Written Opinion dated May 23, 2017", 10 pgs.
"International Application Serial No. PCT/US2017/020792, International Search Report dated Aug. 8, 2017", 8 pgs.
"International Application Serial No. PCT/US2017/020792, Invitation to Pay Add'l Fees and Partial Search Rpt dated May 29, 2017", 16 pgs.
"International Application Serial No. PCT/US2017/020792, Written Opinion dated Aug. 8, 2007", 13 pgs.
Buckley G M, et al., "IRAK-4 inhibitors. Part 1: A series of amides", Bioorganic & Medicinal Chemistry Letters, 18(11), (2008), 3211-3214.
Desai, Bimbisar, et al., "Rapid Discovery of a Novel Series of Abl Kinase Inhibitors by Application of an Integrated Microfluidic Synthesis and Screening Platform", Journal of Medicinal Chemistry, 56(7), (2013), 3033-3047.
Yu, Hana, et al., "1,4-Dihydropyrazolo[4,3-d]imidazoie phenyl derivatives: A novel type II Raf kinase inhibitors", Bioorganic & Medicinal Chemistry Letters, 20(12), (2010), 3805-3808.
"U.S. Appl. No. 15/449,610, Non Final Office Action dated Dec. 19, 2017", 26 pgs.
Cretenet, G, et al., "", 11 Cell Metabolism, (2010), 47-57.
Gupta, S, et al., "", 8 PLoS Biology, (2010), 1-15.
Hetz, C, et al., "", 35 Molecular Cell, (2009), 551-561.
Jabouille, A, et al., "", 6 Oncotarget, (2015), 24922-24934.
Kim, S, et al., "", 194 The Journal of Immunology, (2015), 4498-4506.
Marelli, U K, et al., "", 3 Frontiers in Oncology, (2013), 1-12.
Novab, M, et al., "", 56 Journal of Lipid Research, (2015), 871-887.
Qiu, Q, et al., "", 32 The EMBO Journal, (2013), 2477-2490.
Sha, H, et al., "", 22 Trends in Endocrinology and Metabolism, (2011), 374-381.
Wang, Z, et al., "", 19 Drug Discovery Today, (2014), 145-150.
"U.S. Appl. No. 15/449,610, Response filed May 21, 2018 to Non Final Office Action dated Dec. 19, 2017", 34 pgs.
"International Application Serial No. PCT/US2018/020763, International Search Report dated Jun. 7, 2018", 12 pgs.
"International Application Serial No. PCT/US2018/020763, Written Opinion dated Jun. 7, 2018", 7 pgs.
Dymek, W, et al., "Pyrazole derivatives. II", Acta Poloniae Pharmaceutica Drug Research Polish Pharmaceutical Society Warzsaw PL vol. 22 No. 3, (Jan. 1, 1965), 209-217.
Dymek, W, et al., "Studies on Pyrazole derivatives. I", Acta Poloniae Pharmaceutica Drug Research Polish Pharmaceutical Society Warzsaw PL vol. 21 No. 2, (Jan. 1, 1964), 211-216.
Likun, Wang, et al., "Divergent allosteric control of the IRE1 alpha endoribonuclease using kinase inhibitor", Nature Chemical Biology Nature Publishing Group Basingstoke vol. No. 12, (Dec. 1, 2012), 982-989.

* cited by examiner

SMALL MOLECULE IRE1-α INHIBITORS

CROSS-REFERENCE TO RELATED APPLICATIONS

This application claims the benefit under 35 U.S.C. § 119(e) of U.S. Provisional Patent Application Ser. No. 62/303,951, filed Mar. 4, 2016, and of U.S. Provisional Patent Application Ser. No. 62/303,236, filed Mar. 3, 2016, the disclosures of both of which are incorporated herein in their entirety by reference.

BACKGROUND

Aggressive tumors have evolved strategies that enable them to thrive under constant adverse conditions. Cancer cells respond to hypoxia, nutrient starvation, oxidative stress, and high metabolic demand by adjusting their protein folding capacity via the endoplasmic reticulum (ER) stress response pathway. Cancer patients would benefit from the development of new strategies and therapeutics.

SUMMARY

Described herein are IRE1α inhibitors, compositions containing such inhibitors, and methods of treatment that include administration of such compounds.

The inventors have discovered that XBP1 can promote tumor progression by confounding the development of protective antitumor immunity in the ovarian cancer tumor microenvironment. Without XBP1, tumor resident dendritic cells fail to accumulate intracellular lipids, which normally disrupt effective antigen cross-presentation. This pathological lipid accumulation is fundamentally driven by reactive oxygen species-mediated lipid peroxidation, which directly destabilizes protein-folding chaperones within the endoplasmic reticulum to induce a state of ER stress and XBP1 activation. Additionally, the inventors have found that IRE1α-mediated XBP1 signaling is involved in myeloid cell production of immunosuppressive prostaglandins such as prostaglandin E2 (PGE2).

These findings have led to the development of novel small-molecule IRE1α in inhibitors with the ability to induce two parallel and mutually reinforcing anti-tumor mechanisms, namely the direct inhibition of tumor growth and the simultaneous induction of robust anti-tumor immunity. Such a compound is highly desirable, as no effective, targeted therapies currently exist for either TNBC or ovarian cancer.

Described herein are novel IRE1α kinase inhibitors that exhibit such immune-modulatory properties and/or that allosterically block IRE1alpha endoribonuclease function. The identified direct IRE1α inhibitors have unique chemical structures, unique binding mechanisms, inhibitory activity, and off-target effects.

One aspect of the invention is a compound of formula I:

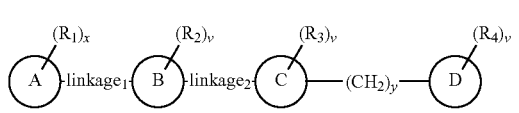

wherein:
A and B are separately each a heterocyclyl ring or a phenyl group, where the A ring has x $R_1$ substituents;
C is phenyl or pyridinyl;
D is heterocyclyl ring;
linkage$_1$ is a single bond between A and B;
linkage$_2$ is a $C_1$-$C_3$ alkylamido, amidoalkyl, amino, urea, alkylurea, or ureaalkyl with a first and second terminal atom;
y is an integer of 0-3, and when y is 0, the linkage between the rings is a single bond;
x is an integer of 0-4;
v is an integer of 0-2;
$R_1$ substituents on the A ring are selected from amino, optionally substituted $C_1$-$C_4$ alkyl, optionally substituted ether, optionally substituted $C_1$-$C_4$ alkoxy, oxy, hydroxy, —NH—SO$_2$-phenyl-($R_5$), and cyano;
$R_2$ substituents on the B ring are selected from amino, and optionally substituted $C_1$-$C_4$ alkyl;
$R_3$ substituents on the C ring are selected from halo, CF$_3$, optionally substituted $C_1$-$C_4$ alkyl, and optionally substituted heteroaryl; and
$R_4$ substituents on the D ring are selected from optionally substituted $C_1$-$C_4$ alkyl, optionally substituted $C_1$-$C_4$ alkoxy, (optionally substituted $C_1$-$C_4$ alkylene)-OH, hydroxy, optionally substituted aryl, optionally substituted benzyl, and optionally substituted benzaldehyde;
$R_5$ is halo; or
a pharmaceutically acceptable salt thereof.

Another aspect of the invention is compound selected from any of the compounds in Tables 1-4, the Examples or a pharmaceutically acceptable salt thereof.

Another aspect of the invention is a composition that includes a carrier and any of the compounds of formula I, pharmaceutically acceptable salts thereof, or any combination of such compounds.

Another aspect of the invention is a composition that includes a carrier and any of the compounds in the Examples, pharmaceutically acceptable salts thereof, or any combination thereof.

Another aspect of the invention is a method that includes administering one or more of such compositions to a mammal. For example, the mammal can be in need of administration of the composition. Such a mammal can, for example, have cancer, a neurodegenerative disease, inflammation, a metabolic disorder, liver dysfunction, brain ischemia, heart ischemia, or an autoimmune disease such as systemic lupus erythematosus. In some cases, the mammal has triple negative breast cancer or ovarian cancer.

The compositions and methods described herein can include one or more agents such as vitamin E, an antioxidant, and/or hydralazine. Such agents can sequester lipid peroxidation byproducts, and can be effective treatments for controlling ER stress responses and sustained IRE1α/XBP1 signaling in tumor-associated dendritic cells exposed, for example, to ovarian cancer-derived ascites.

BRIEF DESCRIPTION OF THE DRAWINGS

In FIG. 2A, the quenching dye is released, fluorescence is emitted.

In FIG. 2B, the quenching dye is retained, and no fluorescence is emitted.

DETAILED DESCRIPTION

Figure 1A:
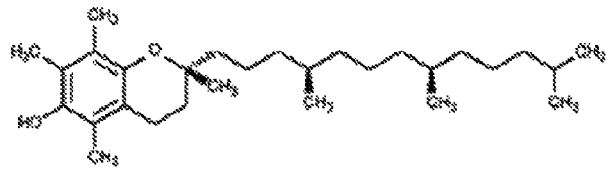
FIG. 1A is the structure of vitamin E (VitE).
Figure 1B:
FIG. 1B is the structure of hydralazine (Hlz), a representative member of lipid peroxidation-sequestering hydrazines.
Figure 1C:
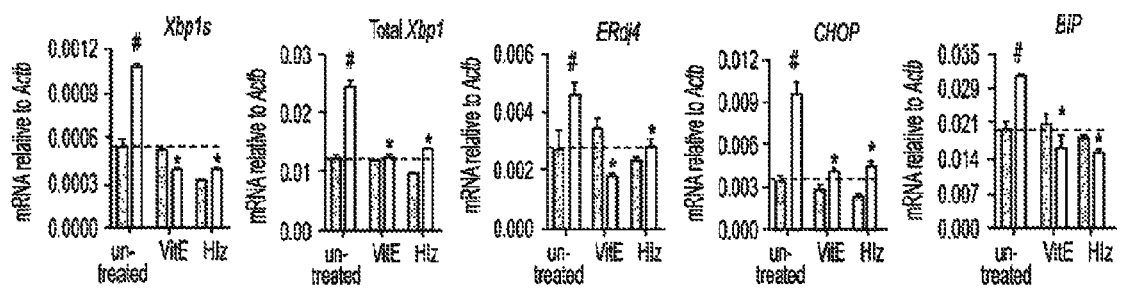
FIG. 1C is RT-qPCR analyses of markers of ER stress after culturing purified tumor-resident DCs in the absence (grey bars) or presence (green bars) of 25% cell-free ovarian cancer ascites supernatants for 18 hours. Data are normalized to Actb expression in each sample.
Figure 1D:
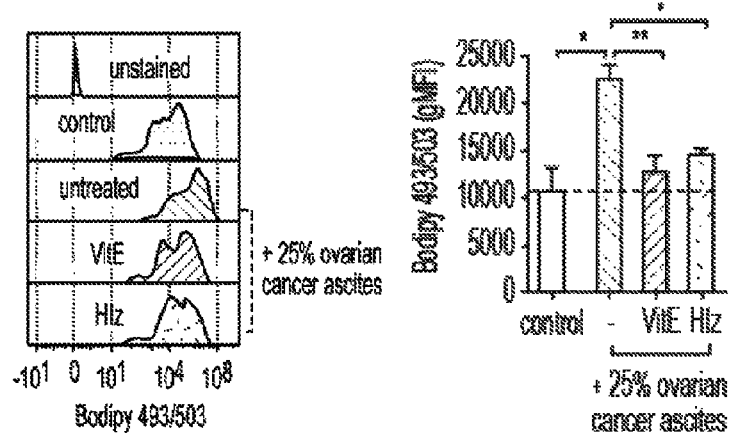
FIG. 1D is flow cytometry analysis of lipid accumulation in mouse bone marrow-derived dendritic cells exposed to the indicated treatments, measured by BODIPY 493/503 staining intensity. Both raw data and quantified geometric mean fluorescence intensity (MFI) are shown.

The invention relates to compounds that can modulate the activity of IRE1α. IRE1α is a type I transmembrane protein with dual enzymatic activities, including an N-terminal domain that projects into the luminal side of the endoplasmic reticulum (IRE1-LD) and a serine/threonine kinase domain plus a C-terminal ribonuclease (RNase) domain located on the cytosolic side of the protein.

The compounds of the invention include any of the compounds described herein, in the Examples, the figures, and Tables 1-4. Embodiments of the invention include but are not limited to one or more compounds of formula I:

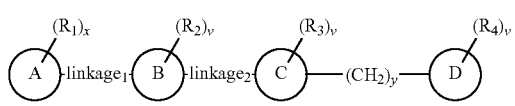

wherein:
A and B are separately each a heterocyclyl ring or a phenyl group, where the A ring has x $R_1$ substituents;
C is phenyl or pyridinyl;
D is heterocyclyl ring;
linkage$_1$ is a single bond between A and B;
linkage$_2$ is a $C_1$-$C_3$ alkylamido, amidoalkyl, amino, urea, alkylurea, or ureaalkyl with a first and second terminal atom;
y is an integer of 0-3, and when y is 0, the linkage between the rings is a single bond;
x is an integer of 0-4;
v is an integer of 0-2;
$R_1$ substituents on the A ring are selected from amino, optionally substituted $C_1$-$C_4$ alkyl, optionally substituted ether, optionally substituted $C_1$-$C_4$ alkoxy, oxy, hydroxy, —NH—SO$_2$-phenyl-($R_5$), and cyano;
$R_2$ substituents on the B ring are selected from amino, and optionally substituted $C_1$-$C_4$ alkyl;
$R_3$ substituents on the C ring are selected from halo, $CF_3$, optionally substituted $C_1$-$C_4$ alkyl, and optionally substituted heteroaryl; and
$R_4$ substituents on the D ring are selected from optionally substituted $C_1$-$C_4$ alkyl, optionally substituted $C_1$-$C_4$ alkoxy, (optionally substituted $C_1$-$C_4$ alkylene)-OH, hydroxy, optionally substituted aryl, optionally substituted benzyl, and optionally substituted benzaldehyde;
$R_5$ is halo; or
a pharmaceutically acceptable salt thereof.

All structures encompassed within a claim are "chemically feasible", by which is meant that the structure depicted by any combination or subcombination of optional substituents meant to be recited h the claim is physically capable of existence with at least some stability as can be determined by the laws of structural chemistry and by experimentation. Structures that are not chemically feasible are not within a claimed set of compounds.

When a substituent is specified to be an atom or atoms of specified identity, "or a bond", a configuration is referred to when the substituent is "a bond" that the groups that are immediately adjacent to the specified substituent are directly connected to each other by a chemically feasible bonding configuration.

In general, "optionally substituted" and "substituent" refers to an organic group as defined herein in which one or more bonds to a hydrogen atom contained therein are optionally replaced by one or more bonds to a non-hydrogen atom such as, but not limited to, a halogen (i.e., "halo" selected from F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', (CH$_2$)$_{0-2}$N(R')N(R')$_2$, N(R')N(R')C(O) R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S) R', N(R)C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. In some cases the R' group is a hydrogen, $C_1$-$C_6$ alkyl, or phenyl.

In many of the compounds described herein, the optional substituents are selected from amino, $C_1$-$C_3$ alkyl, ether, alkoxy, oxy, $CF_3$, and cyano $C_1$-$C_3$ alkoxy, benzyl, and benzaldehyde. The ether and alkoxy groups can have 1-6 carbon atoms.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . ." are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In some embodiments, an alkylene is a $C_1$-$C_3$alkylene. Examples of alkylene groups include, but are not limited to, —CH$_2$—, —CH$_2$CH$_2$—, —CH$_2$CH$_2$CH$_2$—, —CH$_2$CH$_2$CH$_2$CH$_2$—, and the like.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds containing 3 or more ring members, of which one or more is a heteroatom such as, but not limited to, N, O, S, or P. Heteroaryl and heterocyclicalkyl groups are included in the definition of heterocyclyl. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. In some cases, the heterocyclyl is a single ring. In other cases, the heterocyclyl is a fusion of two or three rings. The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl pyrazolyl, triazolyl, tetrazolyl, oxazolyl isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a 6-ring with two carbon atoms and four heteroatoms, and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl(1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[h]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6 indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz, [b,f] azepine-4-yl, 10,11-dihydro-5H-dibenz[b,f]azepine-5-yl), and the like.

Heterocyclylalkyl groups are cyclic alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above.

Heteroarylalkyl groups can be substituted on the heteroaryl moiety, the alkyl moiety, or both.

By a "ring system" or "ring," as the term is used herein, is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" or "amino" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_4$NH wherein each R is independently selected, such as dialkylamines, diarylamines, aralkylamines, heterocyclylamines and the like; and R$_5$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —N(R)$_2$, —N(R)$_3^+$, wherein each R is independently selected, and protonated forms of each. Accordingly, any compound substituted with an amino group can be viewed as an amine.

An "ammonium" ion includes the unsubstituted ammonium ion but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)N(R)$_2$, and —NRC(O)R— groups, respectively. Amide groups therefore include but are not limited to carbamoyl groups (—C(O)NH$_2$) and formamide groups (—NHC(O)H). A "carboxamido" group is a group of the formula C(O)N(R)$_2$, wherein R can be H, alkyl, aryl, etc.

The term "urethane" (or "carbamyl") includes N- and O-urethane groups, i.e., —NRC(O)OR and —OC(O)N(R)$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$).

The term "amidine" or "amidino" includes groups of the formula —C(NR)N(R)$_2$. Typically, an amidino group is —C(NH)NH$_2$.

The term "guanidine" or "guanidino" includes groups of the formula —NRC(NR)N(R)$_2$. Typically, a guanidine group is —NHC(NH)NH$_2$.

"Halo," "halogen," and "halide" include fluorine, chlorine, bromine and iodine.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula I compounds, for example in their purification by recrystallization. All of these salts may be prepared by conventional means from the corresponding compound according to Formula I by reacting, for example, the appropriate acid or base with the compound according to Formula I. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within a mammal's body (e.g., in a patient's body), such as enzymes, to the active pharmaceutical ingredient. Examples of prodrugs include esters of carboxylic acid groups, which can be hydrolyzed by endogenous esterases as are found in the bloodstream of humans and other mammals.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, either per se or as are used in practice of embodiments of the inventive methods, can be any one of any of the combinations and/or sub-combinations of the various embodiments recited.

Provisos may apply to any of the disclosed categories or embodiments wherein any one or more of the other above disclosed embodiments or species may be excluded from such categories or embodiments.

Compounds

The compounds of the invention include any of those described herein, including compounds shown in the Examples. In some instances, the compounds are embraced by formula I:

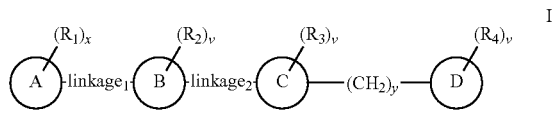

wherein:
A and B are separately each a heterocyclyl ring or a phenyl group, where the A ring has x $R_1$ substituents;
C is phenyl or pyridinyl;
D is heterocyclyl ring;
linkage$_1$ is a single bond between A and B;
linkage$_2$ is a $C_1$-$C_3$ alkylamido, amidoalkyl, amino, urea, alkylurea, or ureaalkyl with a first and second terminal atom;
y is an integer of 0-3, and when y is 0, the linkage between the rings is a single bond;
x is an integer of 0-4;
v is an integer of 0-2;
$R_1$ substituents on the A ring are selected from amino, optionally substituted $C_1$-$C_4$ alkyl, optionally substituted ether, optionally substituted $C_1$-$C_4$ alkoxy, oxy, hydroxy, —NH—$SO_2$-phenyl-($R_5$), and cyano;
$R_2$ substituents on the B ring are selected from amino, and optionally substituted $C_1$-$C_4$ alkyl;

$R_3$ substituents on the C ring are selected from halo, $CF_3$, optionally substituted $C_1$-$C_4$ alkyl, and optionally substituted heteroaryl; and $R_4$ substituents on the D ring are selected from optionally substituted $C_1$-$C_4$ alkyl, optionally substituted $C_1$-$C_4$ alkoxy, (optionally substituted $C_1$-$C_4$ alkylene)-OH, hydroxy, optionally substituted aryl, optionally substituted benzyl, and optionally substituted benzaldehyde;

$R_5$ is halo; or a pharmaceutically acceptable salt thereof.

In some cases, the A ring is heterocyclyl ring. In some cases, the A ring is a heterocyclyl that is a single non-fused ring. In other cases, the A ring is a heterocyclyl that is a fusion of two or three rings. In other cases, the A ring is a heterocyclyl that is a fusion of two rings. In some cases, the A ring of the compounds described herein is heteroaromatic. In some embodiments, the A ring is a single non-fused 5-membered heteroaryl. In some embodiments, the A ring is a single non-fused 6-membered heteroaryl. In some embodiments, the A ring is pyridinyl, pyridazinyl, pyrimidinyl, or pyrazinyl. In some embodiments, the A ring is pyridinyl. In some cases, the A ring is a heteroaryl that is a fusion of two rings. Examples of A rings include indazole, imadazopyridine, imadazopyrazine, imadazopyridazine, pyrrolopyridine, hexahydrothienopyrimidine, imidazole, pyrazole, pyrazine, pyridine, pyrimidine, phenylpyrimidinamine, quinolinyl, isoquinolinyl, tetrahydroquinolinyl, and quinazolinyl. In some embodiments, the A ring is isoquinolinyl. In some embodiments, the A ring is quinazolinyl. For example, the A ring can be selected from any of the following:

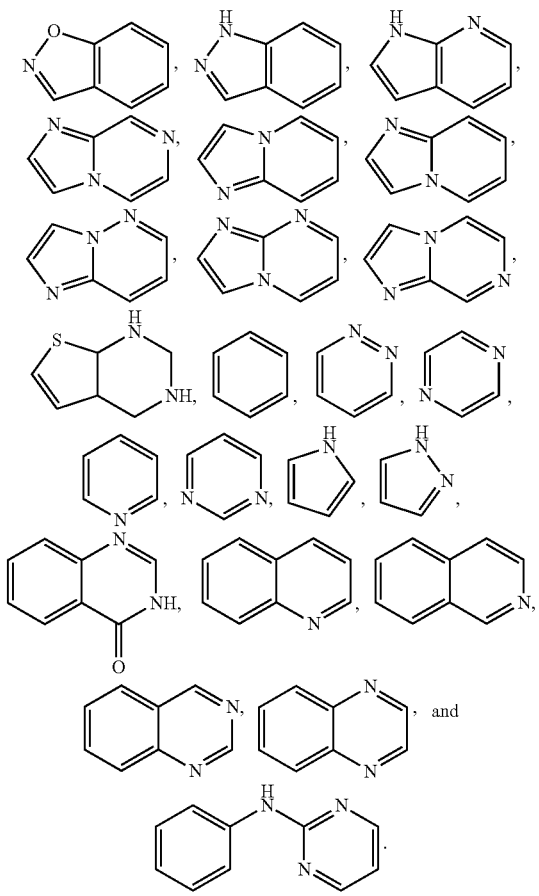

In some instances, the A ring is

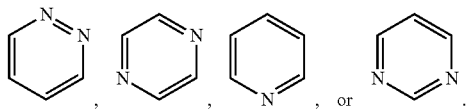

In some instances, the A ring is

In some instances, the A ring is

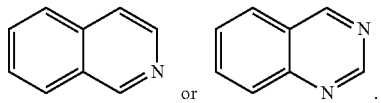

In some embodiments, the $R_1$ substituents on the A ring are selected from amino, optionally substituted $C_1$-$C_4$ alkyl, and hydroxy. In some embodiments, the $R_1$ substituents on the A ring can, for example, be selected from amino and optionally substituted $C_1$-$C_3$ alkyl. In some cases, the $R_1$ substituents on the A ring are selected from —$NH_2$ and —$CH_3$. In addition, in some cases x=0, but in other cases x=1. In some cases, x=2. In some cases, x=3. For example, x can in some cases be 0, 1, or 2 when the A ring is a fusion of two rings. In other cases, x=1 or 2 when the A ring is a single, nonfused ring.

The B ring can be a single, non-fused ring. In some embodiments, the B ring is single, non-fused 5-membered ring. In some embodiments, the B ring is pyrazolyl, imidazolyl, or triazolyl. In some cases, the B ring is pyrazolyl. Alternatively, the B ring can be a fusion of two rings. In some embodiments, the B ring is indazolyl or benzoxazolyl. For example, the B ring can be selected from any of the following:

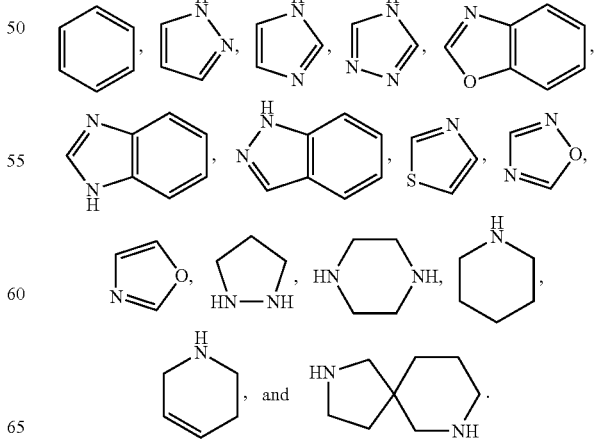

In some cases, the B ring is

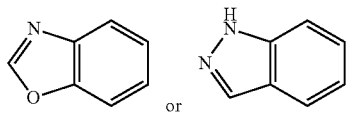 [SMILES: c1ccc2ocnc2c1 ; c1ccc2[nH]ncc2c1]

or

In some cases, the B ring is

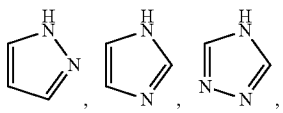

In some cases, the B ring is

In some embodiments, $R_2$ substituents on the B ring are optionally substituted $C_1$-$C_4$ alkyl. In some embodiments, $R_2$ substituents on the B ring are —$CH_3$.

In some cases the C ring can be a phenyl group, and in other cases, a pyridinyl group. In some instances, the C ring is phenyl. In some embodiments, the $R_3$ substituents on the C ring are selected from halo, $CF_3$, optionally substituted $C_1$-$C_4$ alkyl, and optionally substituted heteroaryl. In some embodiments, the $R_3$ substituent is halo. In some embodiments, the $R_3$ substituent is $CF_3$. In some embodiments, the $R_3$ substituent is optionally substituted $C_1$-$C_4$ alkyl. In some embodiments, the $R_3$ substituent is optionally substituted heteroaryl.

The linkage$_2$ group can, for example, be selected from any of the following:

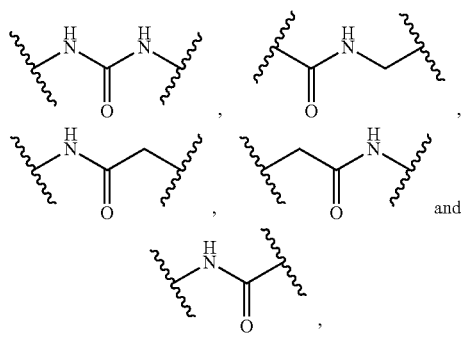

wherein a hydrogen atom on Ring B is replaced by the first terminal atom of linkage$_2$ and a hydrogen atom on Ring C is replaced by the second terminal atom of linkage$_2$. In some cases, linkage$_2$ is

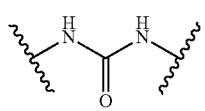

In some cases, linkage$_2$ is

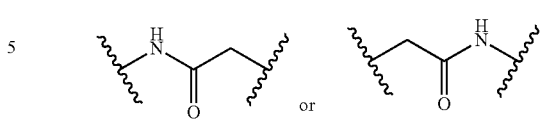

or

In some embodiments, D ring is a heterocyclyl ring containing at least one N atom. In some embodiments, the D ring is piperidinyl, piperazinyl, or morpholinyl. The D ring can, for example, be selected from any of the following:

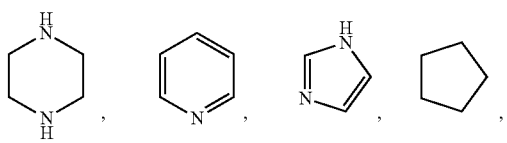

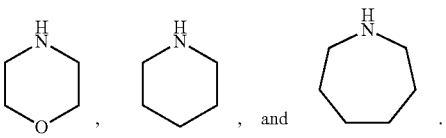

In some embodiments, Ring D is

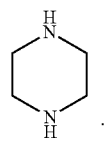

In some embodiments, the $R_4$ substituents on the D ring are optionally substituted $C_1$-$C_4$ alkyl. The $R_4$ substituents on the D ring can in some cases be selected from $CH_3$, $CH_3CHCH_3$, $CH_3CH(CH_2)CH_3$, and $CH_3CH_2CH_3OH$. In some cases, $R_4$ is $CH_3$. In some embodiments, $R_4$ is optionally substituted $C_1$-$C_4$ alkoxy. In some embodiments, $R_4$ is (optionally substituted $C_1$-$C_4$ alkylene)-OH. In some embodiments, $R_4$ is (optionally substituted $C_1$ alkylene)-OH. In some embodiments, $R_4$ is (optionally substituted $C_2$ alkylene)-OH. In some embodiments, $R_4$ is (optionally substituted $C_3$ alkylene)-OH. In some embodiments, $R_4$ is (optionally substituted $C_4$ alkylene)-OH. In some embodiments, $R_4$ is hydroxyl. In some embodiments, $R_4$ is optionally substituted aryl. In some embodiments, $R_4$ is phenyl. In some embodiments, $R_4$ is optionally substituted benzyl. In some embodiments, v is 1. In some embodiments, v is 2. In some embodiments, y is 1. In some embodiments, y is 2. In some embodiments, y is 3.

In some instances, the compounds are embraced by formula Ia:

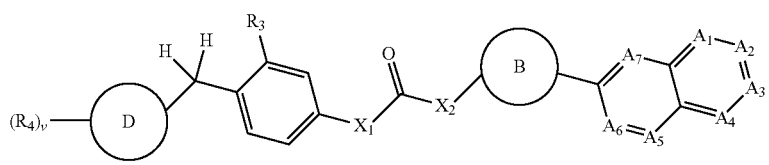

wherein,
A₁ is N, CH, or $CR_1$; $A_2$ is N, CH, or $CR_1$; $A_3$ is N, CH, or $CR_1$; $A_4$ is N, CH, or $CR_1$; $A_5$ is N, CH, or $CR_1$; $A_6$ is N, CH, or $CR_1$; $A_7$ is N CH, or $CR_1$;

v is an integer of 0-2;

Each $R_1$ is $NH_2$ or OH; provided that the number of $R_1$ on the A ring does not exceed 4;

B is selected from:

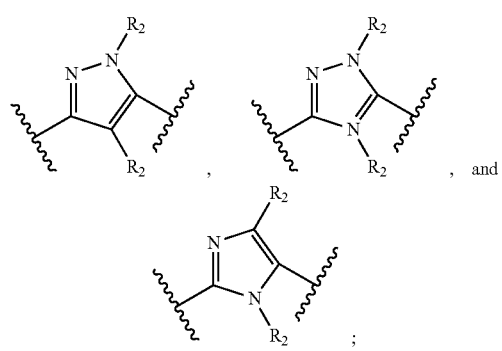

each $R_2$ is independently selected from H and optionally substituted $C_1$-$C_4$ alkyl;

$X_1$ and $X_2$ are each independently $CH_2$ or NH; with the provision that $X_1$ and $X_2$ are not each $CH_2$;

$R_3$ is selected from H, halo, $CF_3$, optionally substituted alkyl, and optionally substituted heteroaryl;

D is heterocyclyl ring containing at least one N atom;

each $R_4$ is selected from H, optionally substituted $C_1$-$C_4$ alkyl, optionally substituted $C_1$-$C_4$ alkoxy, (optionally substituted $C_1$-$C_4$ alkylene)-OH, hydroxy, optionally substituted aryl, and optionally substituted benzyl; or a pharmaceutically acceptable salt thereof.

In some embodiments, $A_1$ is CH or $CR_1$; $A_2$ is N; $A_3$ is CH or $CR_1$; $A_4$ is N, CH, or $CR_1$; $A_5$ is CH or $CR_1$; $A_6$ is CH or $CR_1$; and $A_7$ is CH or $CR_1$. In some embodiments, $A_1$ is CH or $CR_1$; $A_2$ is N; $A_3$ is CH or $CR_1$; $A_4$ is N; $A_5$ is CH or $CR_1$; $A_7$ is CH or $CR_1$; and $A_7$ is CH or $CR_1$. In some embodiments, $A_1$ is CH or $CR_1$; $A_2$ is N; $A_3$ is CH or $CR_1$; $A_4$ is CH or $CR_1$; $A_5$ is CH or $CR_1$; $A_6$ is CH or $CR_1$; and $A_7$ is CH or $CR_1$. In some embodiments, $A_1$ is CH; $A_2$ is N; $A_3$ is $CR_1$; $A_4$ is N; $A_5$ is CH; $A_6$ is CH; and $A_7$ is CH. In some embodiments, $A_1$ is CH; $A_2$ is N; $A_3$ is $CR_1$; $A_4$ is $CR_1$; $A_5$ is CH; $A_6$ is CH; and $A_7$ is CH.

In some embodiments, $A_1$ is CH or $CR_1$; $A_2$ is N; $A_3$ is CH or $CR_1$; $A_4$ is N; $A_5$ is CH; $A_6$ is CH; and $A_7$ is CH. In some embodiments, $A_1$ is CH or $CR_1$; $A_2$ is N; $A_3$ is CH or $CR_1$; $A_4$ is CH or $CR_1$; $A_5$ is CH; $A_6$ is CH; and $A_7$ is CH.

In some embodiments, $A_1$ is N. In some embodiments, $A_1$ is CH. In some embodiments, $A_1$ is $CR_1$, and $R_1$ is OH. In some embodiments, $A_1$ is $CR_1$, and $R_1$ is $NH_2$. In some embodiments, $A_2$ is N. In some embodiments, $A_2$ is CH. In some embodiments, $A_2$ is $CR_1$, and $R_1$ is OH. In some embodiments, $A_2$ is $CR_1$, and $R_1$ is $NH_2$. In some embodiments, $A_3$ is N. In some embodiments, $A_3$ is CH. In some embodiments, $A_3$ is $CR_1$, and $R_1$ is OH. In some embodiments, $A_3$ is $CR_1$, and $R_1$ is $NH_2$. In some embodiments, $A_4$ is N. In some embodiments, $A_4$ is CH. In some embodiments, $A_4$ is $CR_1$, and $R_1$ is OH. In some embodiments, $A_4$ is $CR_1$, and $R_1$ is $NH_2$. In some embodiments, $A_5$ is N. In some embodiments, $A_2$ is CH. In some embodiments, $A_5$ is $CR_1$, and $R_1$ is OH. In some embodiments, $A_5$ is $CR_1$, and $R_1$ is $NH_2$. In some embodiments, $A_6$ is N. In some embodiments, $A_6$ is CH. In some embodiments, $A_6$ is $CR_1$, and $R_1$ is OH. In some embodiments, $A_6$ is $CR_1$, and $R_1$ is $NH_2$. In some embodiments, $A_7$ is N. In some embodiments, $A_7$ is CH. In some embodiments, $A_7$ is $CR_1$, and $R_1$ is OH. In some embodiments, $A_7$ is $CR_1$, and $R_1$ is $NH_2$.

In some embodiments, B is

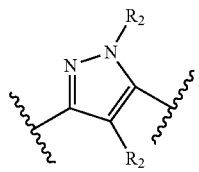

In some embodiments, B is

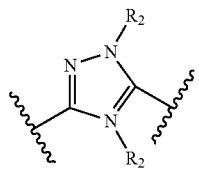

In some embodiments, B is

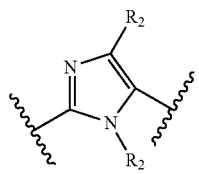

In some embodiments, each $R_2$ is H. In some embodiments, each $R_2$ is optionally substituted $C_1$-$C_4$ alkyl. In some embodiments, each $R_2$ is methyl.

In some embodiments, $X_1$ and $X_2$ are each NH. In some embodiments, $X_1$ is $CH_2$ and $X_2$ is NH. In some embodiments, $X_1$ is NH and $X_2$ is $CH_2$. In some embodiments, $R_3$ is H. In some embodiments, $R_3$ is halo. In some embodiments, $R_3$ is $CF_3$. In some embodiments, $R_3$ is optionally substituted $C_1$-$C_4$ alkyl. In some embodiments, $R_3$ is optionally substituted heteroaryl.

In some embodiments, D is selected from:

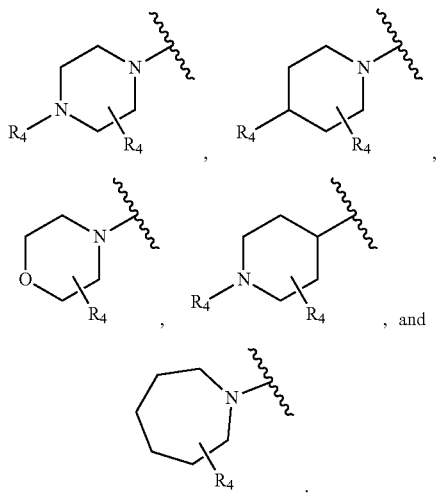

In some embodiments, D is

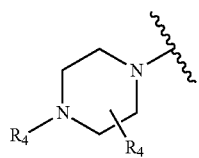

In some embodiments, D is

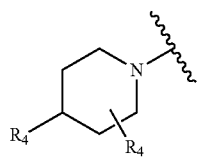

In some embodiments, D is

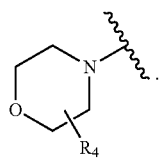

In some embodiments, D is

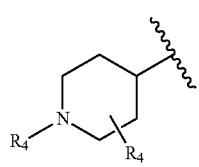

In some embodiments, D is

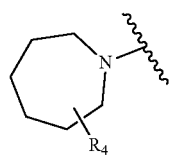

In some embodiments, v is 0. In some embodiments, v is 1. In some embodiments, $R_4$ is H. In some embodiments, $R_4$ is optionally substituted $C_1$-$C_4$ alkyl. In some embodiments, $R_4$ is Me, Et, or i-Pr. In some embodiments, $R_4$ is optionally substituted $C_1$-$C_4$ alkylene)-OH. In some embodiments, $R_4$ is optionally substituted $C_1$alkylene)-OH. In some embodiments, $R_4$ is optionally substituted $C_2$alkylene)-OH. In some embodiments, $R_4$ is optionally substituted $C_3$ alkylene)-OH. In some embodiments, $R_4$ is optionally substituted $C_4$ alkylene)-OH. In some embodiments, $R_4$ is hydroxyl. In some embodiments, $R_4$ is optionally substituted aryl. In some embodiments, $R_4$ is phenyl. In some embodiments, $R_4$ is optionally substituted benzyl. In some embodiments, v is 2. In some embodiments, at least one $R_4$ is H. In some embodiments, at least one $R_4$ is optionally substituted $C_1$-$C_4$ alkyl. In some embodiments, at least one $R_4$ is Me, Et, or i-Pr. In some embodiments, at least one $R_4$ is optionally substituted $C_1$-$C_4$ alkylene)-OH. In some embodiments, at least one $R_4$ is hydroxyl. In some embodiments, at least one $R_4$ is optionally substituted aryl. In some embodiments, at least one $R_4$ is optionally substituted benzyl.

In some instances, the compounds are embraced by formula Ib:

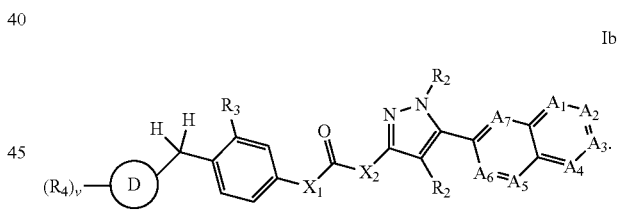

Ib

In some instances, the compounds are embraced by formula Ic:

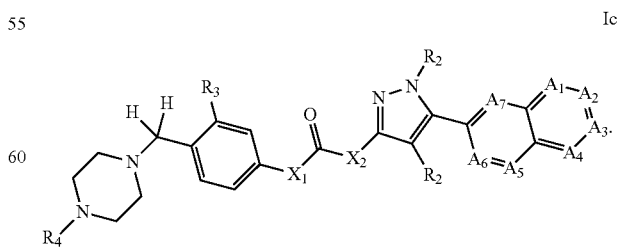

Ic

In some instances, the compounds are embraced by formula Id:

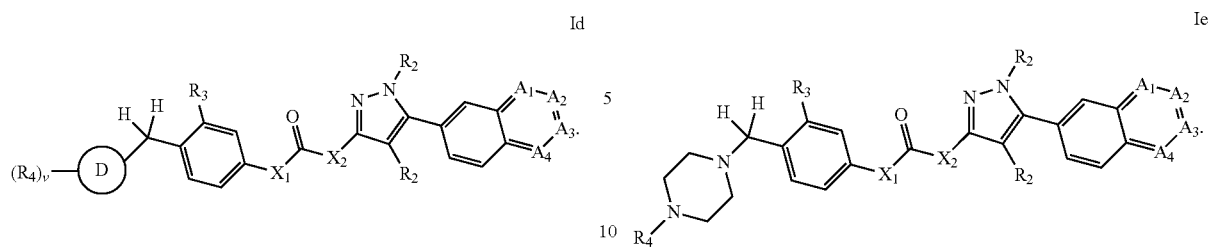

In some instances, the compounds are embraced by formula Ie:

In some instances, the compounds are the compounds as shown in Tables 1, 2, 3, and 4.

TABLE 1

| Compound No. | Structure | Name |
|---|---|---|
| 1 | 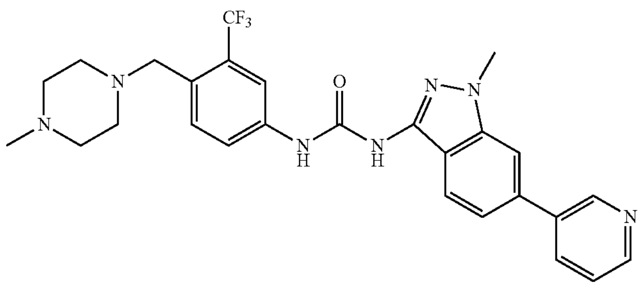 [SMILES: CN1CCN(Cc2ccc(NC(=O)Nc3nn(C)c4cc(-c5cccnc5)ccc34)cc2C(F)(F)F)CC1] | 1-(1-methyl-6-(pyridin-3-yl)-1H-indazol-3-yl)-3-(4-((4-methylpiperazin-1-yl)methyl)-3-(trifluoromethyl)phenyl)urea |
| 2 | 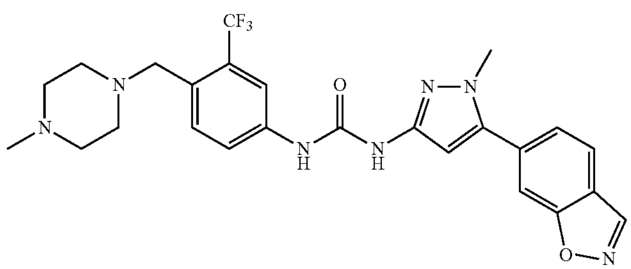 [SMILES: CN1CCN(Cc2ccc(NC(=O)Nc3cc(-c4ccc5cnoc5c4)n(C)n3)cc2C(F)(F)F)CC1] | 1-(5-(benzo[d]isoxazol-6-yl)-1-methyl-1H-pyrazol-3-yl)-3-(4-((4-methylpiperazin-1-yl)methyl)-3-(trifluoromethyl)phenyl)urea |
| 3 | 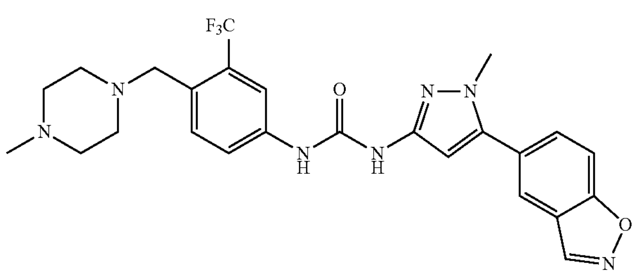 [SMILES: CN1CCN(Cc2ccc(NC(=O)Nc3cc(-c4ccc5oncc5c4)n(C)n3)cc2C(F)(F)F)CC1] | 1-(5-(benzo[d]isoxazol-5-yl)-1-methyl-1H-pyrazol-3-yl)-3-(4-((4-methylpiperazin-1-yl)methyl)-3-(trifluoromethyl)phenyl)urea |
| 4 | 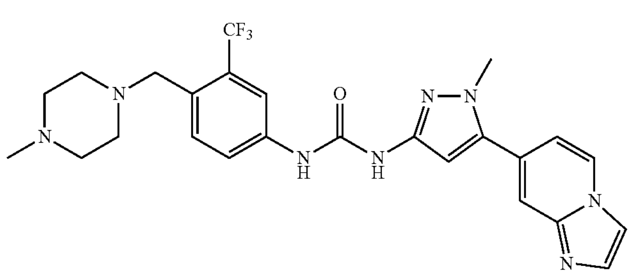 [SMILES: CN1CCN(Cc2ccc(NC(=O)Nc3cc(-c4ccn5ccnc5c4)n(C)n3)cc2C(F)(F)F)CC1] | 1-(5-(imidazo[1,2-a]pyridin-7-yl)-1-methyl-1H-pyrazol-3-yl)-3-(4-((4-methylpiperazin-1-yl)methyl)-3-(trifluoromethyl)phenyl)urea |

TABLE 1-continued

| Compound No. | Structure | Name |
|---|---|---|
| 5 | 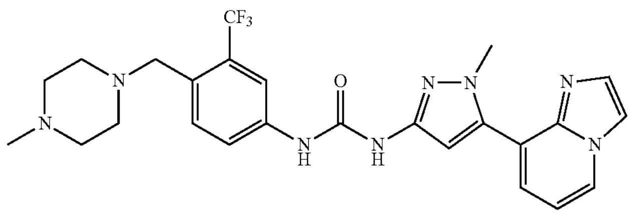 [SMILES: CN1CCN(Cc2ccc(NC(=O)Nc3cc(-c4cccn5ccnc45)n(C)n3)cc2C(F)(F)F)CC1] | 1-(5-(imidazo[1,2-a]pyridin-8-yl)-1-methyl-1H-pyrazol-3-yl)-3-(4-((4-methylpiperazin-1-yl)methyl)-3-(trifluoromethyl)phenyl)urea |
| 6 | 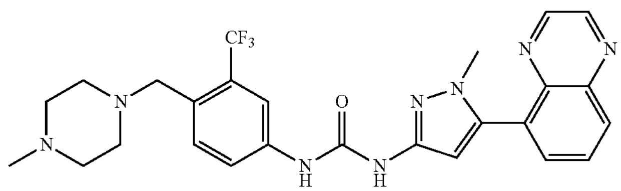 [SMILES: CN1CCN(Cc2ccc(NC(=O)Nc3cc(-c4cccc5nccnc45)n(C)n3)cc2C(F)(F)F)CC1] | 1-(1-methyl-5-(quinoxalin-5-yl)-1H-pyrazol-3-yl)-3-(4-((4-methylpiperazin-1-yl)methyl)-3-trifluoromethyl)phenyl)urea |
| 7 | 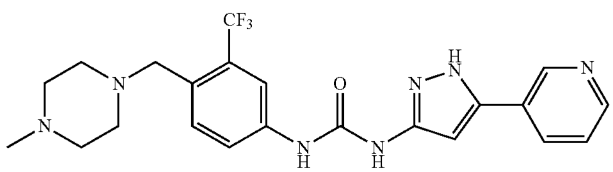 [SMILES: CN1CCN(Cc2ccc(NC(=O)Nc3cc(-c4cccnc4)[nH]n3)cc2C(F)(F)F)CC1] | 1-(4-((4-methylpiperazin-1-yl)methyl)-3-(trifluoromethyl)phenyl)-3-(5-(pyridin-3-yl)-1H-pyrazol-3-yl)urea |
| 8 | 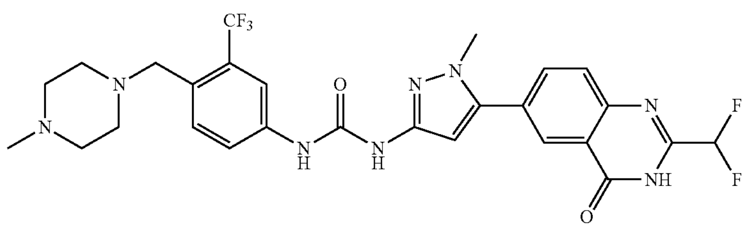 [SMILES: CN1CCN(Cc2ccc(NC(=O)Nc3cc(-c4ccc5nc(C(F)F)[nH]c(=O)c5c4)n(C)n3)cc2C(F)(F)F)CC1] | 1-(5-(2-(difluoromethyl)-4-oxo-3,4-dihydroquinazolin-6-yl)-1-methyl-1H-pyrazol-3-yl)-3-(4-((4-methylpiperazin-1-yl)methyl)-3-(trifluoromethyl)phenyl)urea |
| 9 | 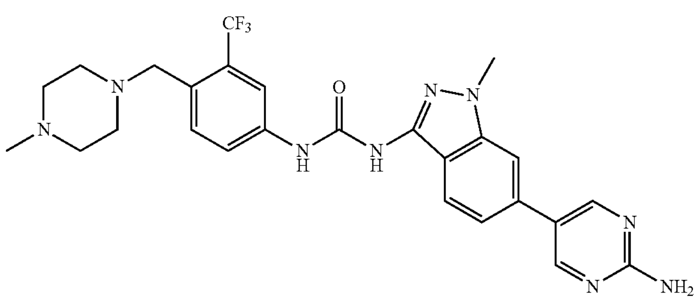 [SMILES: CN1CCN(Cc2ccc(NC(=O)Nc3nn(C)c4cc(-c5cnc(N)nc5)ccc34)cc2C(F)(F)F)CC1] | 1-(6-(2-aminopyrimidin-5-yl)-1-methyl-1H-indazol-3-yl)-3-(4-((4-methylpiperazin-1-yl)methyl)-3-(trifluoromethyl)phenyl)urea |
| 10 | 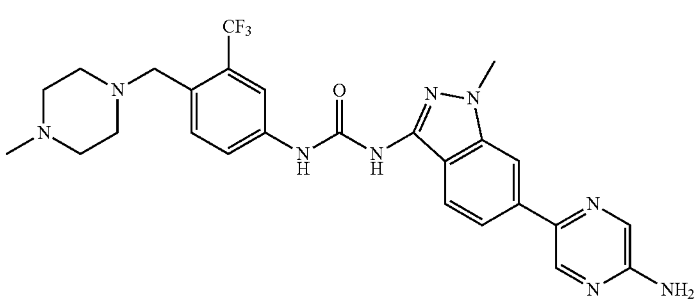 [SMILES: CN1CCN(Cc2ccc(NC(=O)Nc3nn(C)c4cc(-c5cnc(N)cn5)ccc34)cc2C(F)(F)F)CC1] | 1-(6-(5-aminopyrazin-2-yl)-1-methyl-1H-indazol-3-yl)-3-(4-((4-methylpiperazin-1-yl)methyl)-3-(trifluoromethyl)phenyl)urea |

TABLE 1-continued

| Compound No. | Structure | Name |
|---|---|---|
| 11 | 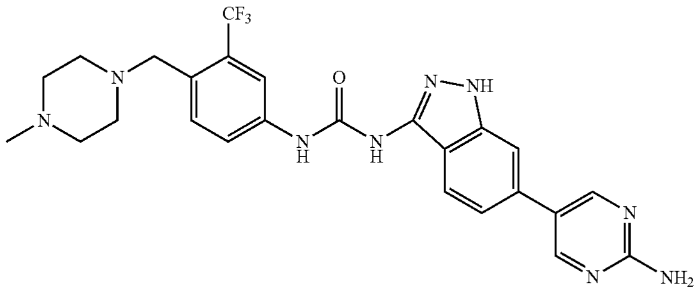 [SMILES: CN1CCN(Cc2ccc(NC(=O)Nc3n[nH]c4cc(-c5cnc(N)nc5)ccc34)cc2C(F)(F)F)CC1] | 1-(6-(2-aminopyrimidin-5-yl)-1H-indazol-3-yl)-3-(4-((4-methylpiperazin-1-yl)methyl)-3-(trifluoromethyl)phenyl)urea |
| 12 | 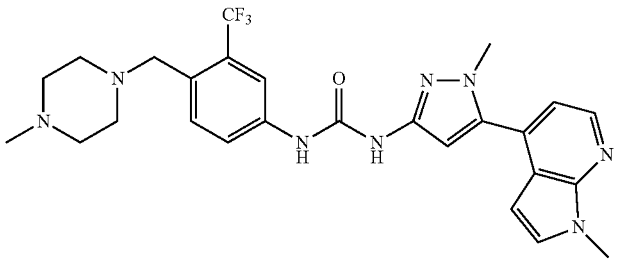 | 1-(1-methyl-5-(1-methyl-1H-pyrrolo[2,3-b]pyridin-4-yl)-1H-pyrazol-3-yl)-3-(4-((4-methylpiperazin-1-yl)methyl)-3-(trifluoromethyl)phenyl)urea |
| 13 | 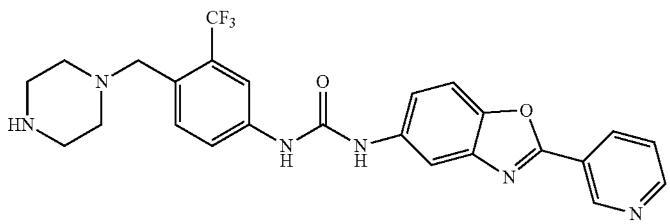 [SMILES: O=C(Nc1ccc(CN2CCNCC2)c(C(F)(F)F)c1)Nc1ccc2oc(-c3cccnc3)nc2c1] | 1-(4-(piperazin-1-ylmethyl)-3-(trifluoromethyl)phenyl)-3-(2-(pyridin-3-yl)benzo[d]oxazol-5-yl)urea |
| 14 | 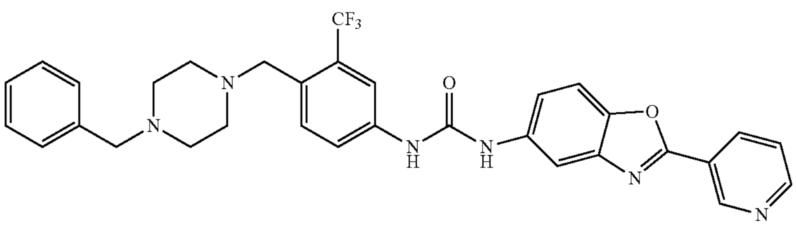 [SMILES: O=C(Nc1ccc(CN2CCN(Cc3ccccc3)CC2)c(C(F)(F)F)c1)Nc1ccc2oc(-c3cccnc3)nc2c1] | 1-(4-((4-benzylpiperazin-1-yl)methyl)-3-(trifluoromethyl)phenyl)-3-(2-(pyridin-3-yl)benzo[d]oxazol-5-yl)urea |
| 15 | 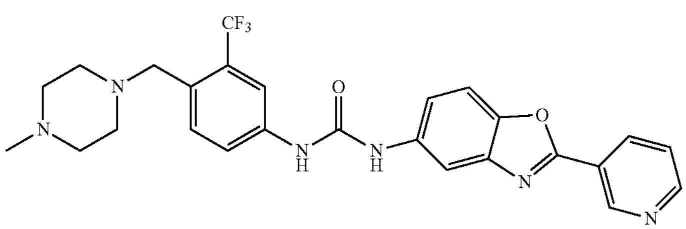 [SMILES: CN1CCN(Cc2ccc(NC(=O)Nc3ccc4oc(-c5cccnc5)nc4c3)cc2C(F)(F)F)CC1] | 1-(4-((4-methylpiperazin-1-yl)methyl)-3-(trifluoromethyl)phenyl)-3-(2-(pyridin-3-yl)benzo[d]oxazol-5-yl)urea |
| 16 | 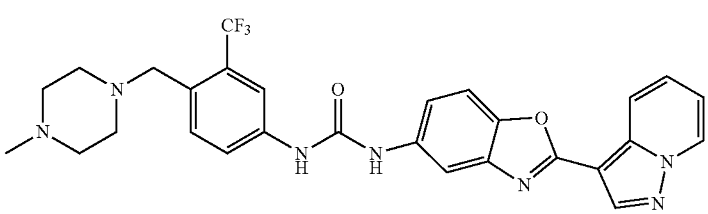 [SMILES: CN1CCN(Cc2ccc(NC(=O)Nc3ccc4oc(-c5cnn6ccccc56)nc4c3)cc2C(F)(F)F)CC1] | 1-(4-((4-methylpiperazin-1-yl)methyl)-3-(trifluoromethyl)phenyl)-3-(2-(pyrazolo[1,5-a]pyridin-3-yl)benzo[d]oxazol-5-yl)urea |

TABLE 1-continued

| Compound No. | Structure | Name |
|---|---|---|
| 17 | 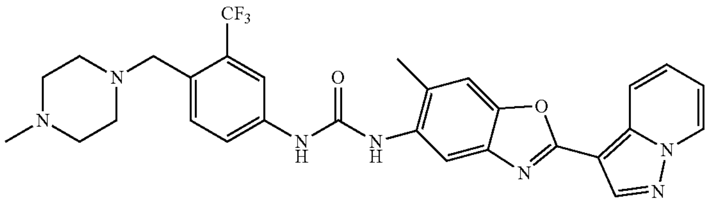 [SMILES: Cc1cc2oc(-c3cnn4ccccc34)nc2cc1NC(=O)Nc1ccc(CN2CCN(C)CC2)c(C(F)(F)F)c1] | 1-(6-methyl-2-(pyrazolo[1,5-a]pyridin-3-yl)benzo[d]oxazol-5-yl)-3-(4-((4-methylpiperazin-1-yl)methyl)-3-(trifluoromethyl)phenyl)urea |
| 18 | 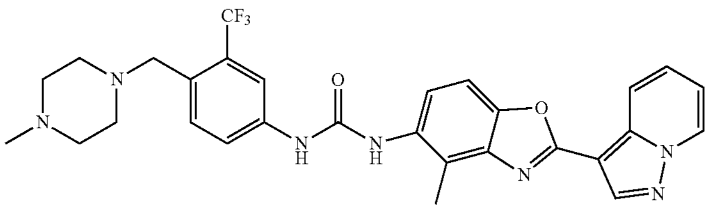 [SMILES: Cc1c(NC(=O)Nc2ccc(CN3CCN(C)CC3)c(C(F)(F)F)c2)ccc2oc(-c3cnn4ccccc34)nc12] | 1-(4-methyl-2-(pyrazolo[1,5-a]pyridin-3-yl)benzo[d]oxazol-5-yl)-3-(4-((4-methylpiperazin-1-yl)methyl)-3-(trifluoromethyl)phenyl)urea |
| 19 | 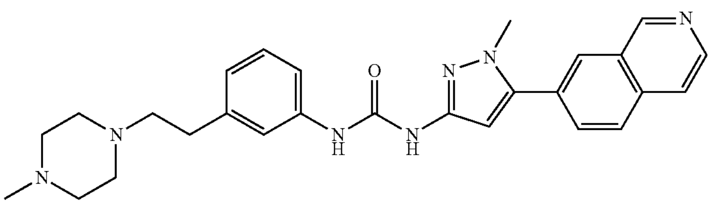 [SMILES: CN1CCN(CCc2cccc(NC(=O)Nc3cc(-c4ccc5ccncc5c4)n(C)n3)c2)CC1] | 1-(5-(isoquinolin-7-yl)-1-methyl-1H-pyrazol-3-yl)-3-(3-(2-(4-methylpiperazin-1-yl)ethyl)phenyl)urea |
| 20 | 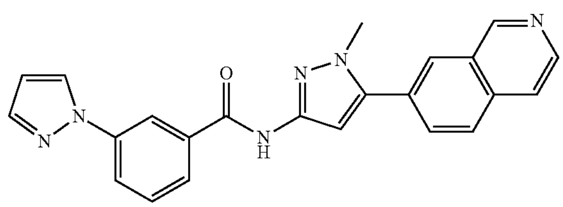 [SMILES: Cn1nc(NC(=O)c2cccc(-n3cccn3)c2)cc1-c1ccc2ccncc2c1] | N-(5-(isoquinolin-7-yl)-1-methyl-1H-pyrazol-3-yl)-3-(1H-pyrazol-1-yl)benzamide |
| 21 | 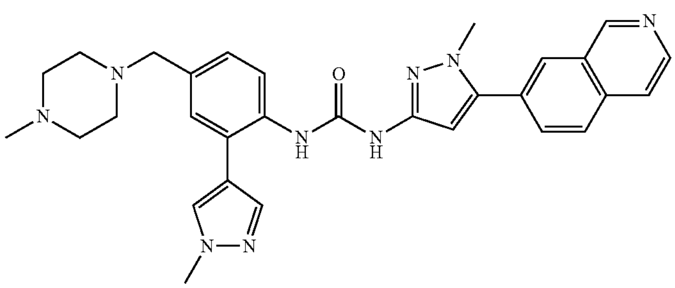 [SMILES: CN1CCN(Cc2ccc(NC(=O)Nc3cc(-c4ccc5ccncc5c4)n(C)n3)c(-c3cnn(C)c3)c2)CC1] | 1-(5-(isoquinolin-7-yl)-1-methyl-1H-pyrazol-3-yl)-3-(2-(1-methyl-1H-pyrazol-4-yl)-4-((4-methylpiperazin-1-yl)methyl)phenyl)urea |

TABLE 2

| Compound No. | Structure | Name |
|---|---|---|
| 22 | 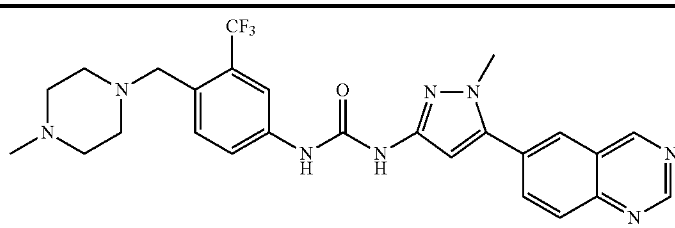 | 1-(1-methyl-5-(quinazolin-6-yl)-1H-pyrazol-3-yl)-3-(4-((4-methylpiperazin-1-yl)methyl)-3-(trifluoromethyl)phenyl)urea |

TABLE 2-continued

| Compound No. | Structure | Name |
|---|---|---|
| 23 | 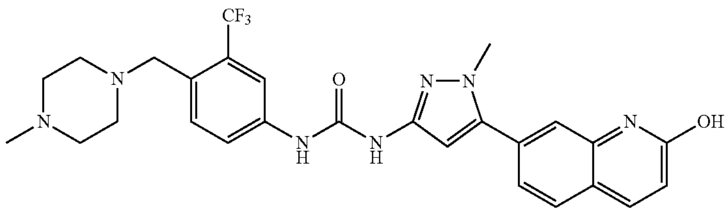 [SMILES: CN1CCN(Cc2ccc(NC(=O)Nc3cc(-c4ccc5ccc(O)nc5c4)n(C)n3)cc2C(F)(F)F)CC1] | 1-(5-(2-hydroxyquinolin-7-yl)-1-methyl-1H-pyrazol-3-yl)-3-(4-((4-methylpiperazin-1-yl)methyl)-3-(trifluoromethyl)phenyl)urea |
| 24 | 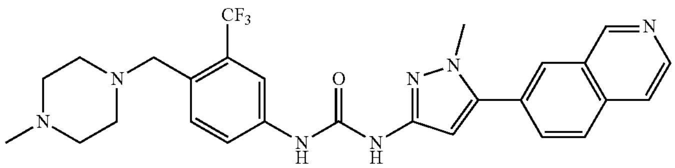 | 1-(5-(isoquinolin-7-yl)-1-methyl-1H-pyrazol-3-yl)-3-(4-((4-methylpiperazin-1-yl)methyl)-3-(trifluoromethyl)phenyl)urea |
| 25 | 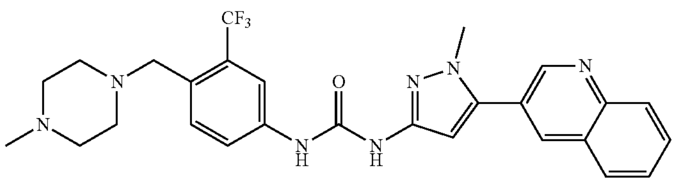 [SMILES: CN1CCN(Cc2ccc(NC(=O)Nc3cc(-c4cnc5ccccc5c4)n(C)n3)cc2C(F)(F)F)CC1] | 1-(1-methyl-5-(quinolin-3-yl)-1H-pyrazol-3-yl)-3-(4-((4-methylpiperazin-1-yl)methyl)-3-(trifluoromethyl)phenyl)urea |
| 26 | 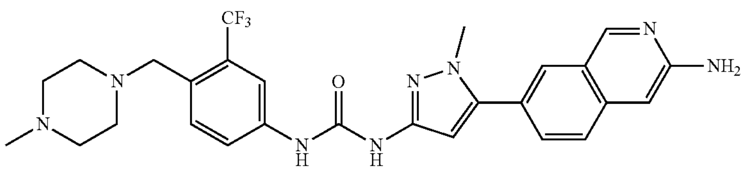 [SMILES: CN1CCN(Cc2ccc(NC(=O)Nc3cc(-c4ccc5cc(N)ncc5c4)n(C)n3)cc2C(F)(F)F)CC1] | 1-(5-(3-aminoisoquinolin-7-yl)-1-methyl-1H-pyrazol-3-yl)-3-(4-((4-methylpiperazin-1-yl)methyl)-3-(trifluoromethyl)phenyl)urea |
| 27 | 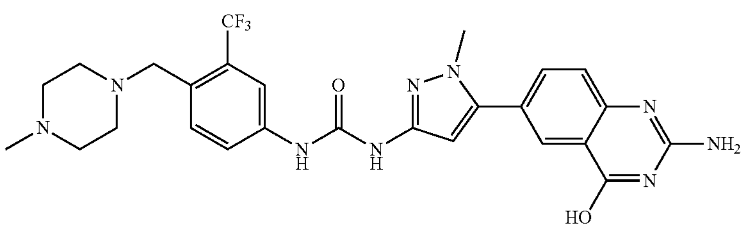 [SMILES: CN1CCN(Cc2ccc(NC(=O)Nc3cc(-c4ccc5nc(N)nc(O)c5c4)n(C)n3)cc2C(F)(F)F)CC1] | 1-(5-(2-amino-4-hydroxyquinazolin-6-yl)-1-methyl-1H-pyrazol-3-yl)-3-(4-((4-methylpiperazin-1-yl)methyl)-3-(trifluoromethyl)phenyl)urea |
| 28 | 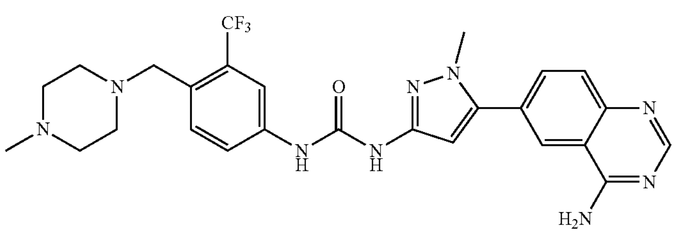 [SMILES: CN1CCN(Cc2ccc(NC(=O)Nc3cc(-c4ccc5ncnc(N)c5c4)n(C)n3)cc2C(F)(F)F)CC1] | 1-(5-(4-aminoquinazolin-6-yl)-1-methyl-1H-pyrazol-3-yl)-3-(4-((4-methylpiperazin-1-yl)methyl)-3-(trifluoromethyl)phenyl)urea |
| 29 | 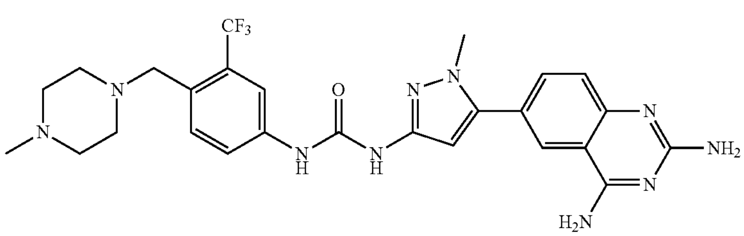 [SMILES: CN1CCN(Cc2ccc(NC(=O)Nc3cc(-c4ccc5nc(N)nc(N)c5c4)n(C)n3)cc2C(F)(F)F)CC1] | 1-(5-(2,4-diaminoquinazolin-6-yl)-1-methyl-1H-pyrazol-3-yl)-3-(4-((4-methylpiperazin-1-yl)methyl)-3-(trifluoromethyl)phenyl)urea |

TABLE 2-continued

| Compound No. | Structure | Name |
|---|---|---|
| 30 | 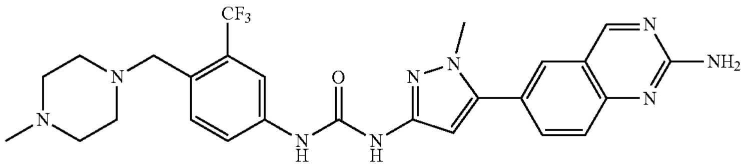 [SMILES: CN1CCN(Cc2ccc(NC(=O)Nc3cc(-c4ccc5nc(N)ncc5c4)n(C)n3)cc2C(F)(F)F)CC1] | 1-(5-(2-aminoquinazolin-6-yl)-1-methyl-1H-pyrazol-3-yl)-3-(4-((4-methylpiperazin-1-yl)methyl)-3-(trifluoromethyl)phenyl)urea |
| 31 | 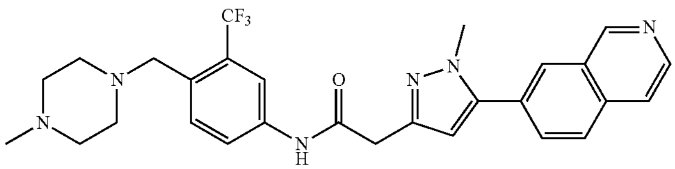 [SMILES: CN1CCN(Cc2ccc(NC(=O)Cc3cc(-c4ccc5ccncc5c4)n(C)n3)cc2C(F)(F)F)CC1] | 2-(5-(isoquinolin-7-yl)-1-methyl-1H-pyrazol-3-yl)-N-(4-((4-methylpiperazin-1-yl)methyl)-3-(trifluoromethyl)phenyl)acetamide |
| 32 | 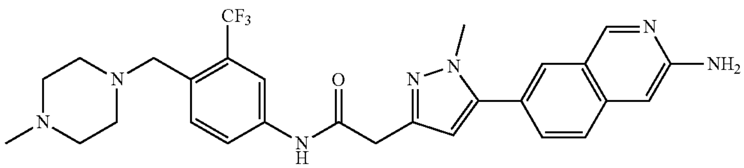 [SMILES: CN1CCN(Cc2ccc(NC(=O)Cc3cc(-c4ccc5nc(N)ncc5c4)n(C)n3)cc2C(F)(F)F)CC1] | 2-(5-(3-aminoisoquinolin-7-yl)-1-methyl-1H-pyrazol-3-yl)-N-(4-((4-methylpiperazin-1-yl)methyl)-3-(trifluoromethyl)phenyl)acetamide |
| 33 | 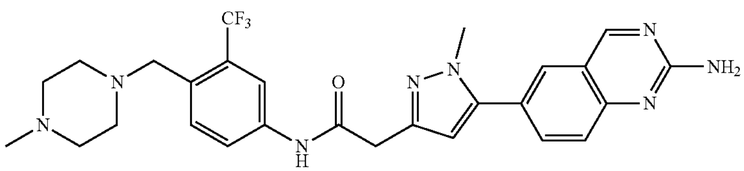 | 2-(5-(2-aminoquinazolin-6-yl)-1-methyl-1H-pyrazol-3-yl)-N-(4-((4-methylpiperazin-1-yl)methyl)-3-(trifluoromethyl)phenyl)acetamide |
| 34 | 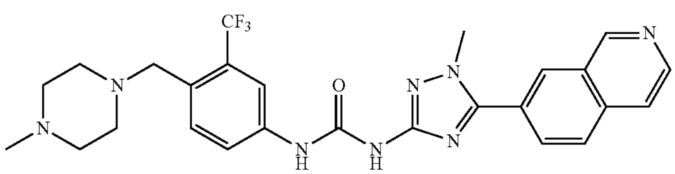 | 1-(5-(isoquinolin-7-yl)-1-methyl-1H-1,2,4-triazol-3-yl)-3-(4-((4-methylpiperazin-1-yl)methyl)-3-(trifluoromethyl)phenyl)urea |
| 35 | 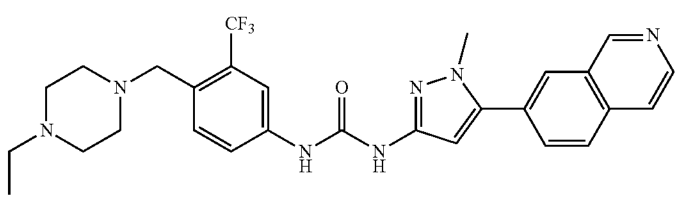 [SMILES: CCN1CCN(Cc2ccc(NC(=O)Nc3cc(-c4ccc5ccncc5c4)n(C)n3)cc2C(F)(F)F)CC1] | 1-(4-((4-ethylpiperazin-1-yl)methyl)-3-(trifluoromethyl)phenyl)-3-(5-(isoquinolin-7-yl)-1-methyl-1H-pyrazol-3-yl)urea |
| 36 | 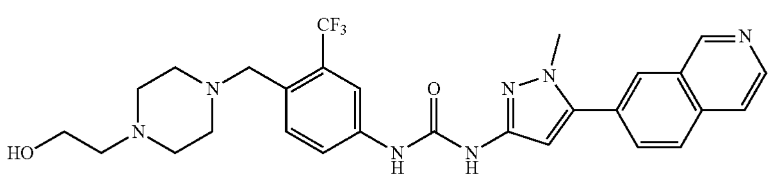 [SMILES: Cn1nc(NC(=O)Nc2ccc(CN3CCN(CCO)CC3)c(C(F)(F)F)c2)cc1-c1ccc2ccncc2c1] | 1-(4-((4-(2-hydroxyethyl)piperazin-1-yl)methyl)-3-(trifluoromethyl)phenyl)-3-(5-(isoquinolin-7-yl)-1-methyl-1H-pyrazol-3-yl)urea |
| 37 | 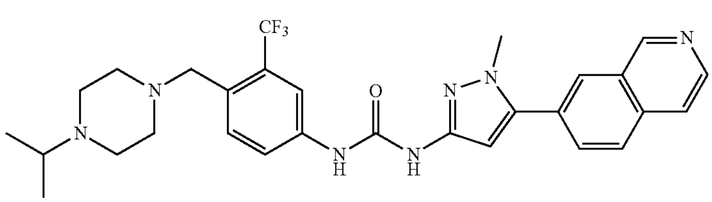 [SMILES: CC(C)N1CCN(Cc2ccc(NC(=O)Nc3cc(-c4ccc5ccncc5c4)n(C)n3)cc2C(F)(F)F)CC1] | 1-(4-((4-isopropylpiperazin-1-yl)methyl)-3-(trifluoromethyl)phenyl)-3-(5-(isoquinolin-7-yl)-1-methyl-1H-pyrazol-3-yl)urea |

TABLE 2-continued

| Compound No. | Structure | Name |
|---|---|---|
| 38 | 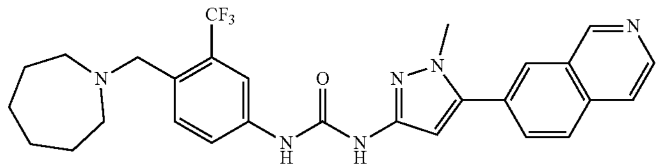 [SMILES: Cn1nc(NC(=O)Nc2ccc(CN3CCCCCC3)c(C(F)(F)F)c2)cc1-c1ccc2ccncc2c1] | 1-(4-(azepan-1-ylmethyl)-3-(trifluoromethyl)phenyl)-3-(5-(isoquinolin-7-yl)-1-methyl-1H-pyrazol-3-yl)urea |
| 39 | 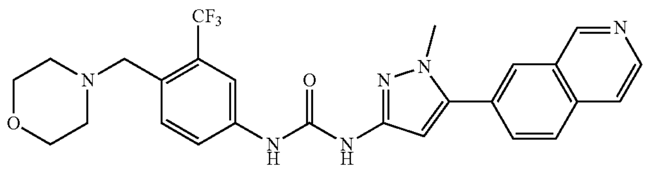 [SMILES: Cn1nc(NC(=O)Nc2ccc(CN3CCOCC3)c(C(F)(F)F)c2)cc1-c1ccc2ccncc2c1] | 1-(5-(isoquinolin-7-yl)-1-methyl-1H-pyrazol-3-yl)-3-(4-(morpholinomethyl)-3-(trifluoromethyl)phenyl)urea |
| 40 | 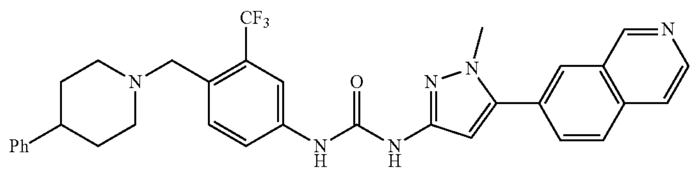 [SMILES: Cn1nc(NC(=O)Nc2ccc(CN3CCC(c4ccccc4)CC3)c(C(F)(F)F)c2)cc1-c1ccc2ccncc2c1] | 1-(5-(isoquinolin-7-yl)-1-methyl-1H-pyrazol-3-yl)-3-(4-((4-phenylpiperidin-1-yl)methyl)-3-(trifluoromethyl)phenyl)urea |
| 41 | 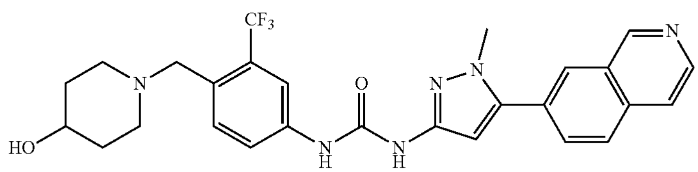 [SMILES: Cn1nc(NC(=O)Nc2ccc(CN3CCC(O)CC3)c(C(F)(F)F)c2)cc1-c1ccc2ccncc2c1] | 1-(4-((4-hydroxypiperidin-1-yl)methyl)-3-(trifluoromethyl)phenyl)-3-(5-(isoquinolin-7-yl)-1-methyl-1H-pyrazol-3-yl)urea |
| 42 | 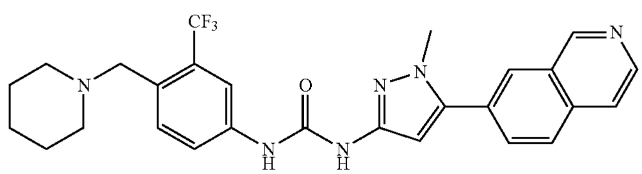 [SMILES: Cn1nc(NC(=O)Nc2ccc(CN3CCCCC3)c(C(F)(F)F)c2)cc1-c1ccc2ccncc2c1] | 1-(5-(isoquinolin-7-yl)-1-methyl-1H-pyrazol-3-yl)-3-(4-(piperidin-1-ylmethyl)-3-(trifluoromethyl)phenyl)urea |
| 43 | 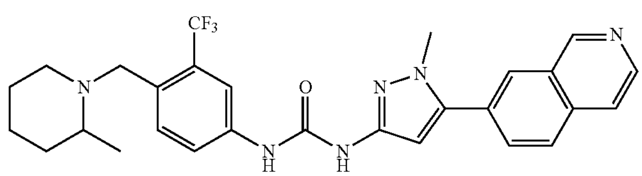 [SMILES: CC1CCCCN1Cc1ccc(NC(=O)Nc2cc(-c3ccc4ccncc4c3)n(C)n2)cc1C(F)(F)F] | 1-(5-(isoquinolin-7-yl)-1-methyl-1H-pyrazol-3-yl)-3-(4-((2-methylpiperidin-1-yl)methyl)-3-(trifluoromethyl)phenyl)urea |
| 44 | 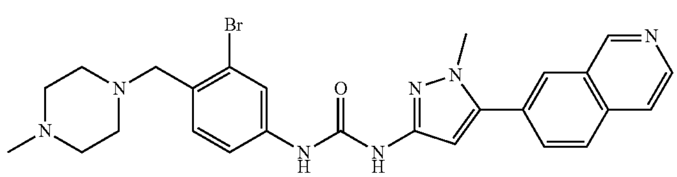 | 1-(3-bromo-4-((4-methylpiperazin-1-yl)methyl)phenyl)-3-(5-(isoquinolin-7-yl)-1-methyl-1H-pyrazol-3-yl)urea |
| 45 | 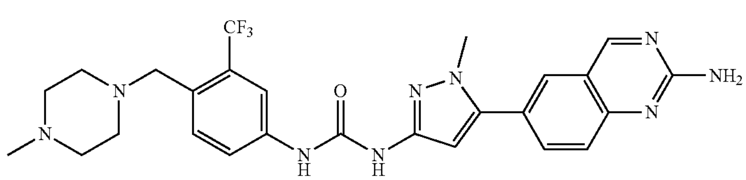 | 1-(5-(2-aminoquinazolin-6-yl)-1-methyl-1H-1,2,4-triazol-3-yl)-3-(4-((4-methylpiperazin-1-yl)methyl)-3-(trifluoromethyl)phenyl)urea |

TABLE 2-continued

| Compound No. | Structure | Name |
|---|---|---|
| 46 | 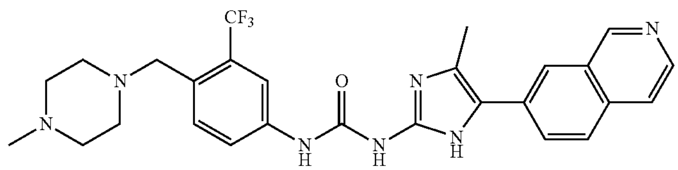 [SMILES: Cc1nc(NC(=O)Nc2ccc(CN3CCN(C)CC3)c(C(F)(F)F)c2)[nH]c1-c1ccc2ccncc2c1] | 1-(5-(isoquinolin-7-yl)-4-methyl-4H-imidazol-2-yl)-3-(4-((4-methylpiperazin-1-yl)methyl)-3-(trifluoromethyl)phenyl)urea |
| 47 | 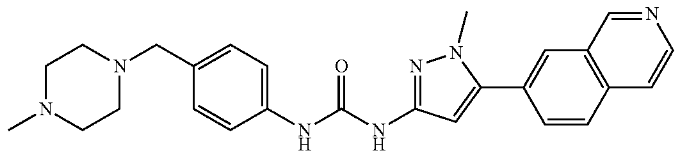 [SMILES: CN1CCN(Cc2ccc(NC(=O)Nc3cc(-c4ccc5ccncc5c4)n(C)n3)cc2)CC1] | 1-(5-(isoquinolin-7-yl)-1-methyl-1H-pyrazol-3-yl)-3-(4-((4-methylpiperazin-1-yl)methyl)phenyl)urea |
| 48 | 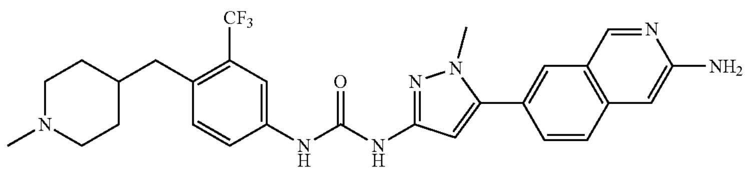 [SMILES: CN1CCC(Cc2ccc(NC(=O)Nc3cc(-c4ccc5cc(N)ncc5c4)n(C)n3)cc2C(F)(F)F)CC1] | 1-(5-(3-aminoisoquinolin-7-yl)-1-methyl-1H-pyrazol-3-yl)-3-(4-((1-methylpiperidin-4-yl)methyl)-3-(trifluoromethyl)phenyl)urea |
| 49 | 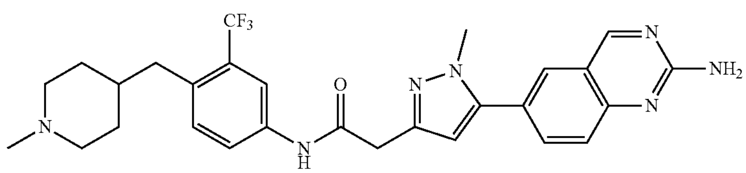 [SMILES: CN1CCC(Cc2ccc(NC(=O)Cc3cc(-c4ccc5nc(N)ncc5c4)n(C)n3)cc2C(F)(F)F)CC1] | 2-(5-(2-aminoquinazolin-6-yl)-1-methyl-1H-pyrazol-3-yl)-N-(4-((1-methylpiperidin-4-yl)methyl)-3-(trifluoromethyl)phenyl)acetamide |
| 50 | 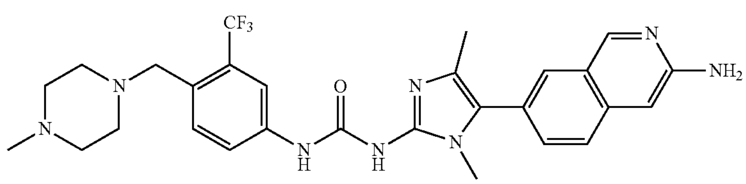 [SMILES: Cc1nc(NC(=O)Nc2ccc(CN3CCN(C)CC3)c(C(F)(F)F)c2)n(C)c1-c1ccc2cc(N)ncc2c1] | 1-(5-(3-aminoisoquinolin-7-yl)-1,4-dimethyl-1H-imidazol-2-yl)-3-(4-((4-methylpiperazin-1-yl)methyl)-3-(trifluoromethyl)phenyl)urea |
| 51 | 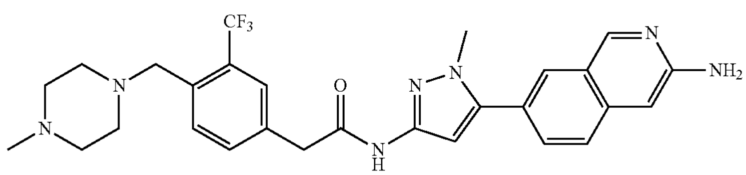 [SMILES: CN1CCN(Cc2ccc(CC(=O)Nc3cc(-c4ccc5cc(N)ncc5c4)n(C)n3)cc2C(F)(F)F)CC1] | N-(5-(3-aminoisoquinolin-7-yl)-1-methyl-1H-pyrazol-3-yl)-2-(4-((4-methylpiperazin-1-yl)methyl)-3-(trifluoromethyl)phenyl)acetamide |
| 52 | 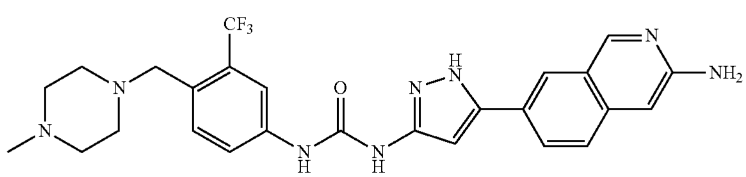 | 1-(5-(3-aminoisoquinolin-7-yl)-1H-pyrazol-3-yl)-3-(4-((4-methylpiperazin-1-yl)methyl)-3-(trifluoromethyl)phenyl)urea |

TABLE 3

| Compound No. | Structure | Name |
|---|---|---|
| 53 | 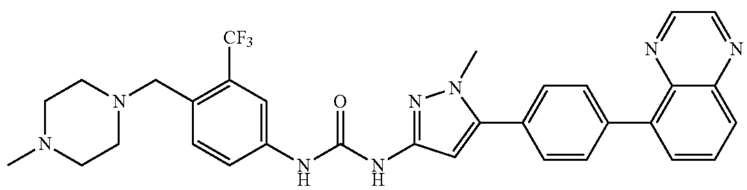 | 1-(1-methyl-5-(4-(quinoxalin-5-yl)phenyl)-1H-pyrazol-3-yl)-3-(4-((4-methylpiperazin-1-yl)methyl)-3-trifluoromethyl)phenyl)urea |
| 54 | 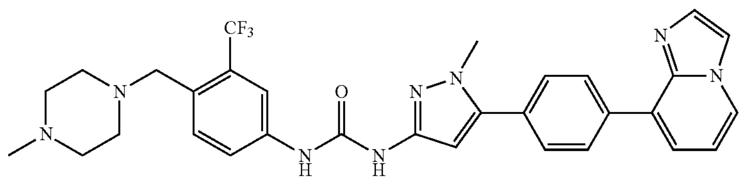 | 1-(5-(4-(imidazo[1,2-a]pyridin-8-yl)phenyl)-1-methyl-1H-pyrazol-3-yl)-3-(4-((4-methylpiperazin-1-yl)methyl)-3-(trifluoromethyl)phenyl)urea |
| 55 | 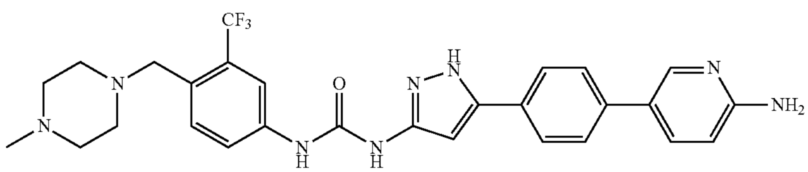 | 1-(5-(4-(6-aminopyridin-3-yl)phenyl)-1H-pyrazol-3-yl)-3-(4-((4-methylpiperazin-1-yl)methyl)-3-(trifluoromethyl)phenyl)urea |
| 56 | 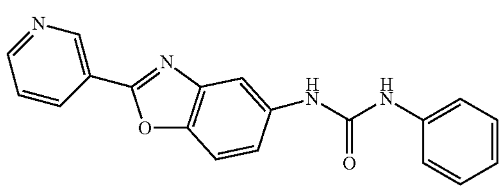 [SMILES: O=C(Nc1ccccc1)Nc1ccc2oc(-c3cccnc3)nc2c1] | 1-phenyl-3-(2-(pyridin-3-yl)benzo[d]oxazol-5-yl)urea |
| 57 | 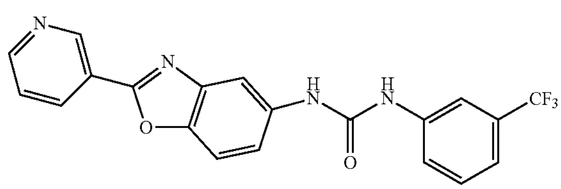 [SMILES: O=C(Nc1cccc(C(F)(F)F)c1)Nc1ccc2oc(-c3cccnc3)nc2c1] | 1-(2-(pyridin-3-yl)benzo[d]oxazol-5-yl)-3-(3-(trifluoromethyl)phenyl)urea |
| 58 | 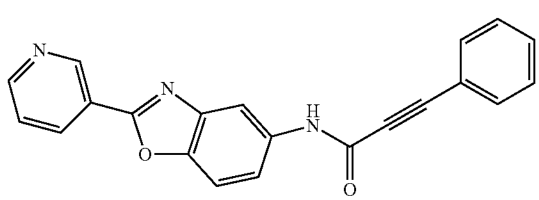 [SMILES: O=C(C#Cc1ccccc1)Nc1ccc2oc(-c3cccnc3)nc2c1] | 3-phenyl-N-(2-(pyridin-3-yl)benzo[d]oxazol-5-yl)propiolamide |
| 59 | 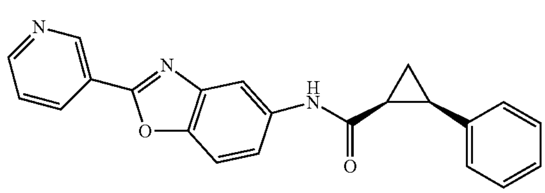 [SMILES: O=C(Nc1ccc2oc(-c3cccnc3)nc2c1)[C@H]1C[C@H]1c1ccccc1] | (1S,2R)-2-phenyl-N-(2-(pyridin-3-yl)benzo[d]oxazol-5-yl)cyclopropane-1-carboxamide |

TABLE 3-continued

| Compound No. | Structure | Name |
|---|---|---|
| 60 | 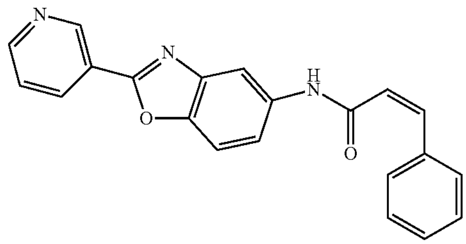 [SMILES: O=C(/C=C\c1ccccc1)Nc1ccc2oc(-c3cccnc3)nc2c1] | (Z)-3-phenyl-N-(2-(pyridin-3-yl)benzo[d]oxazol-5-yl)acrylamide |
| 61 | 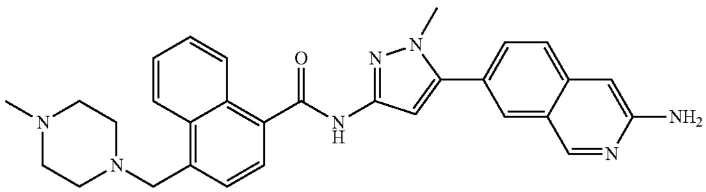 | N-(5-(3-aminoisoquinolin-7-yl)-1-methyl-1H-pyrazol-3-yl)-4-((4-methylpiperazin-1-yl)methyl)-1-naphthamide |
| 62 | 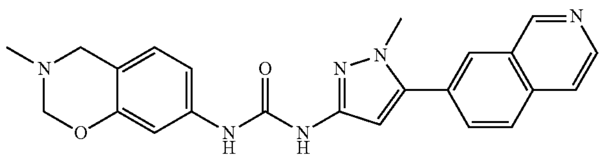 [SMILES: CN1COc2cc(NC(=O)Nc3cc(-c4ccc5ccncc5c4)n(C)n3)ccc2C1] | 1-(5-(isoquinolin-7-yl)-1-methyl-1H-pyrazol-3-yl)-3-(3-methyl-3,4-dihydro-2H-benzo[e][1,3]oxazin-7-yl)urea |
| 63 | 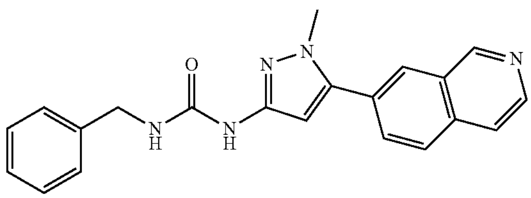 [SMILES: Cn1nc(NC(=O)NCc2ccccc2)cc1-c1ccc2ccncc2c1] | 1-benzyl-3-(5-(isoquinolin-7-yl)-1-methyl-1H-pyrazol-3-yl)urea |
| 64 | 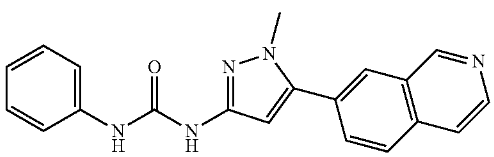 [SMILES: Cn1nc(NC(=O)Nc2ccccc2)cc1-c1ccc2ccncc2c1] | 1-(5-(isoquinolin-7-yl)-1-methyl-1H-pyrazol-3-yl)-3-phenylurea |
| 65 | 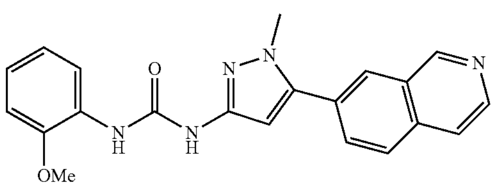 [SMILES: COc1ccccc1NC(=O)Nc1cc(-c2ccc3ccncc3c2)n(C)n1] | 1-(5-(isoquinolin-7-yl)-1-methyl-1H-pyrazol-3-yl)-3-(2-methoxyphenyl)urea |
| 66 | 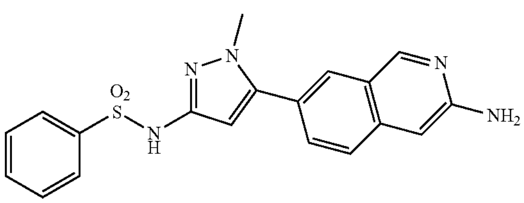 | N-(5-(3-aminoisoquinolin-7-yl)-1-methyl-1H-pyrazol-3-yl)benzenesulfonamide |
| 67 | 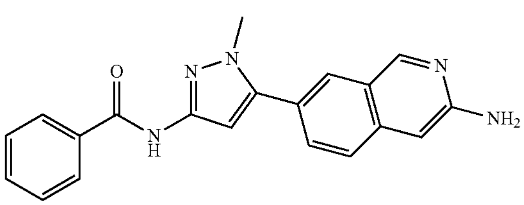 [SMILES: Cn1nc(NC(=O)c2ccccc2)cc1-c1ccc2cc(N)ncc2c1] | N-(5-(3-aminoisoquinolin-7-yl)-1-methyl-1H-pyrazol-3-yl)benzamide |

TABLE 3-continued

| Compound No. | Structure | Name |
|---|---|---|
| 68 | 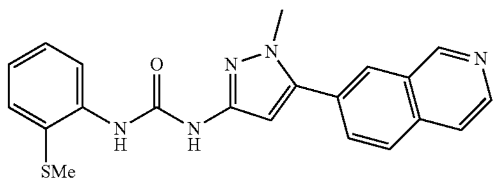 [SMILES: CSc1ccccc1NC(=O)Nc1cc(-c2ccc3ccncc3c2)n(C)n1] | 1-(5-(isoquinolin-7-yl)-1-methyl-1H-pyrazol-3-yl)-3-(2-(methylthio)phenyl)urea |
| 69 | 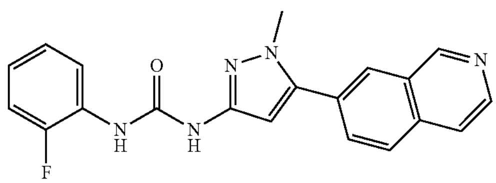 [SMILES: Cn1nc(NC(=O)Nc2ccccc2F)cc1-c1ccc2ccncc2c1] | 1-(2-fluorophenyl)-3-(5-(isoquinolin-7-yl)-1-methyl-1H-pyrazol-3-yl)urea |
| 70 | 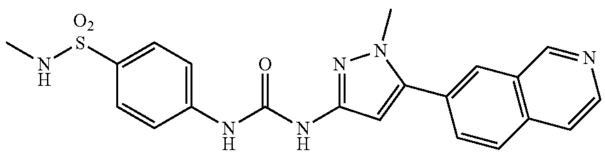 | 4-(3-(5-(isoquinolin-7-yl)-1-methyl-1H-pyrazol-3-yl)ureido)-N-methylbenzenesulfonamide |
| 71 | 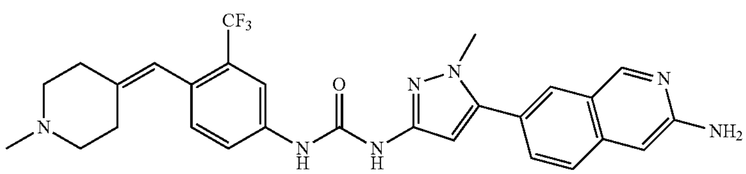 [SMILES: CN1CCC(=Cc2ccc(NC(=O)Nc3cc(-c4ccc5cc(N)ncc5c4)n(C)n3)cc2C(F)(F)F)CC1] | 1-(5-(3-aminoisoquinolin-7-yl)-1-methyl-1H-pyrazol-3-yl)-3-(4-((1-methylpiperidin-4-ylidene)methyl)-3-(trifluoromethyl)phenyl)urea |
| 72 | 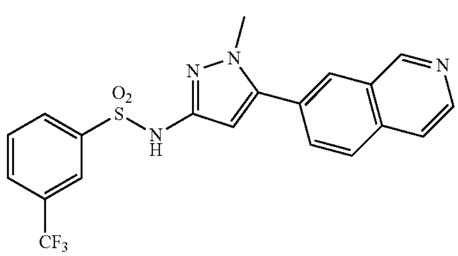 | N-(5-(isoquinolin-7-yl)-1-methyl-1H-pyrazol-3-yl)-3-(trifluoromethyl)benzenesulfonamide |
| 73 | 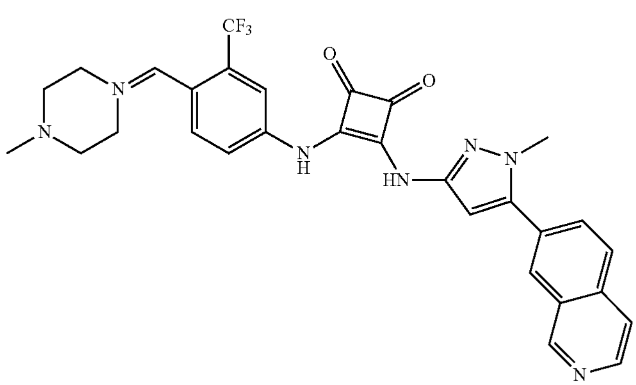 | 3-((5-(isoquinolin-7-yl)-1-methyl-1H-pyrazol-3-yl)amino)-4-((4-((4-methylpiperazin-1-yl)methyl)-3-(trifluoromethyl)phenyl)amino)cyclobut-3-ene-1,2-dione |

TABLE 3-continued

| Compound No. | Structure | Name |
|---|---|---|
| 74 | 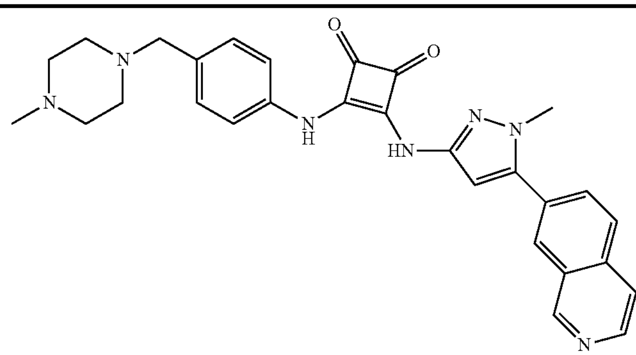 | 3-((5-(isoquinolin-7-yl)-1-methyl-1H-pyrazol-3-yl)amino)-4-((4-((4-methylpiperazin-1-yl)methyl)phenyl)amino)cyclobut-3-ene-1,2-dione |
| 75 | 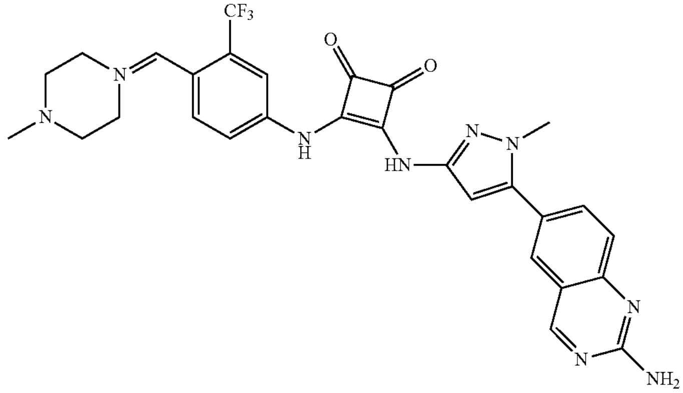 | 3-((5-(2-aminoquinazolin-6-yl)-1-methyl-1H-pyrazol-3-yl)amino)-4-((4-((4-methylpiperazin-1-yl)methyl)-3-(trifluoromethyl)phenyl)amino)cyclobut-3-ene-1,2-dione |
| 76 | 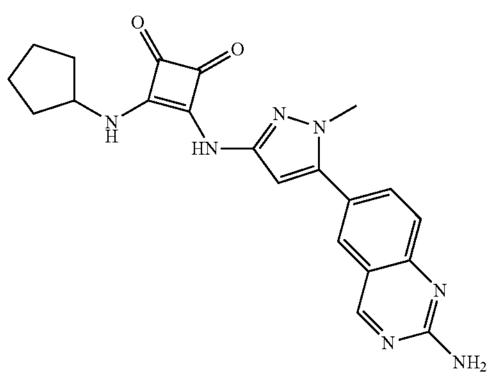 [SMILES: Cn1nc(Nc2c(NC3CCCC3)c(=O)c2=O)cc1-c1ccc2nc(N)ncc2c1] | 3-((5-(2-aminoquinazolin-6-yl)-1-methyl-1H-pyrazol-3-yl)amino)-4-(cyclopentylamino)cyclobut-3-ene-1,2-dione |

TABLE 4

| Compound No. | Structure |
|---|---|
| 77 | 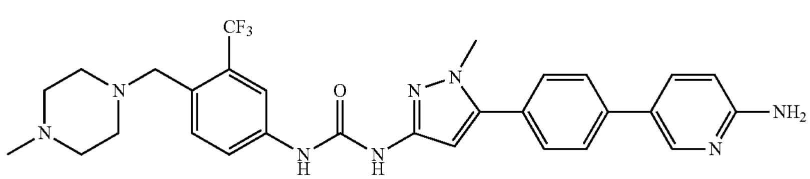 |

TABLE 4-continued

| Compound No. | Structure |
|---|---|
| 78 | 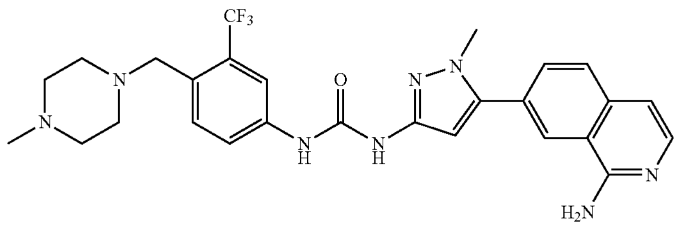 |
| 79 | 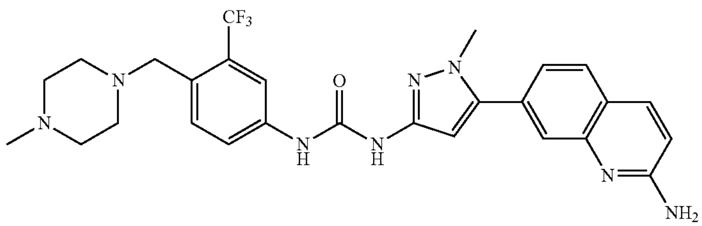 |
| 80 | 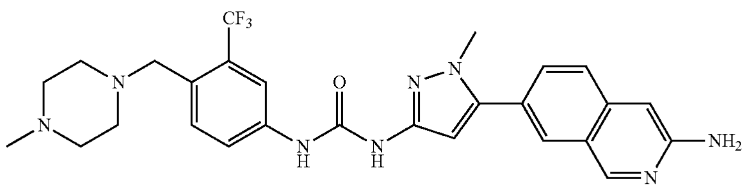 |
| 81 | 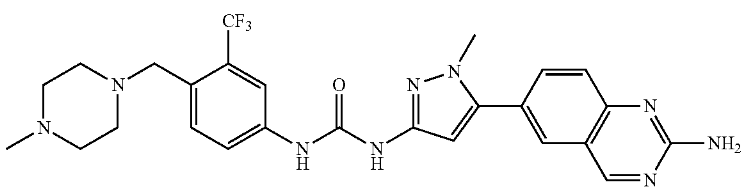 |
| 82 | 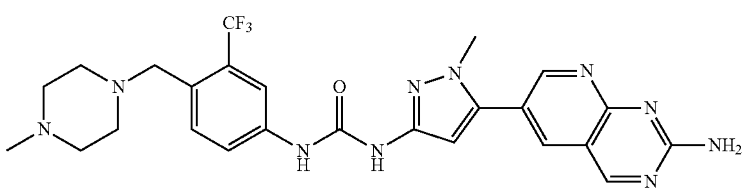 |
| 83 | 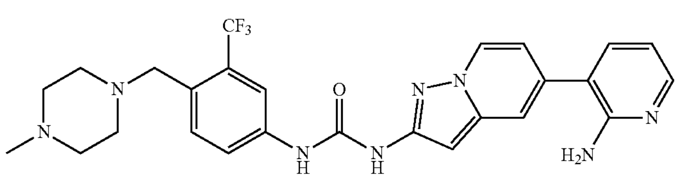 [SMILES: CN1CCN(Cc2ccc(NC(=O)Nc3cc4cc(-c5cccnc5N)ccn4n3)cc2C(F)(F)F)CC1] |
| 84 | 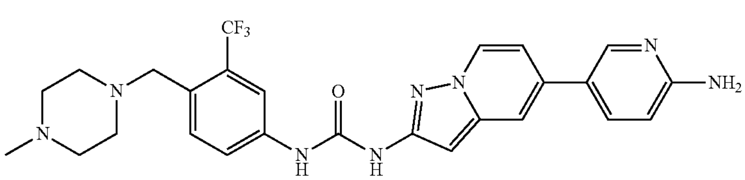 [SMILES: CN1CCN(Cc2ccc(NC(=O)Nc3cc4cc(-c5ccc(N)nc5)ccn4n3)cc2C(F)(F)F)CC1] |
| 85 | 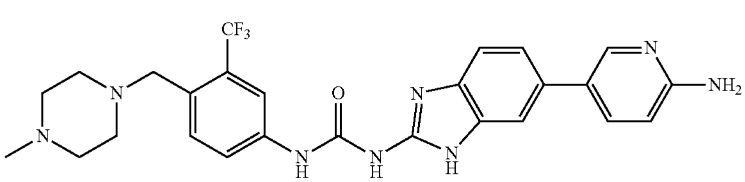 [SMILES: CN1CCN(Cc2ccc(NC(=O)Nc3nc4ccc(-c5ccc(N)nc5)cc4[nH]3)cc2C(F)(F)F)CC1] |

TABLE 4-continued
| Compound No. | Structure |
|---|---|
| 86 | 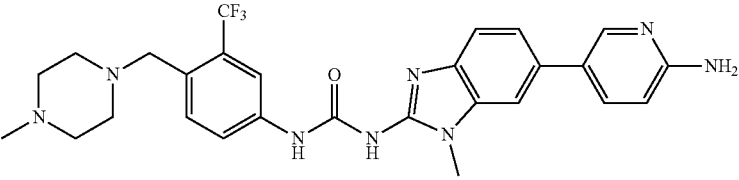 [SMILES: CN1CCN(Cc2ccc(NC(=O)Nc3nc4ccc(-c5ccc(N)nc5)cc4n3C)cc2C(F)(F)F)CC1] |
| 87 | 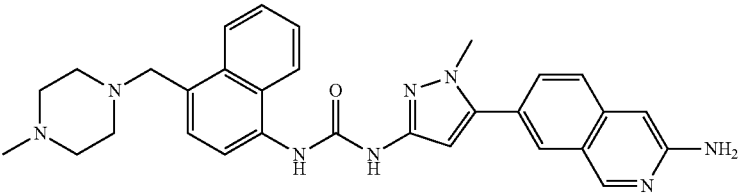 |
| 88 | 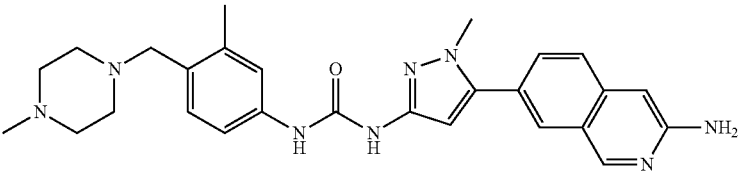 |
| 89 | 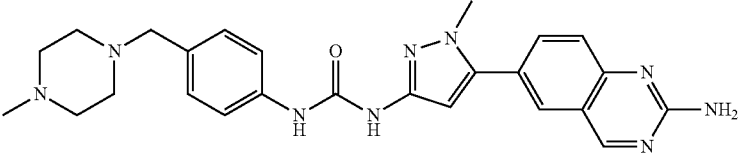 |
| 90 | 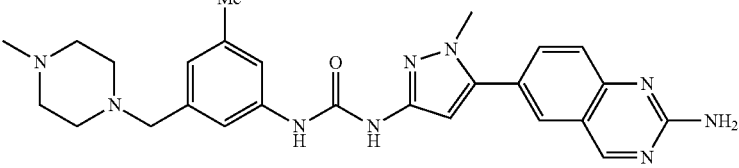 |
| 91 | 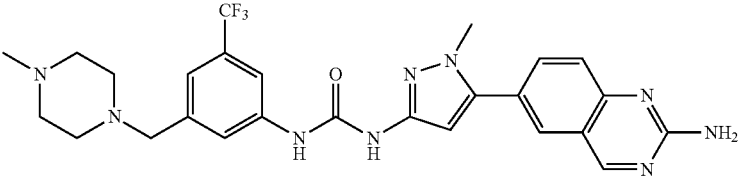 |
| 92 | 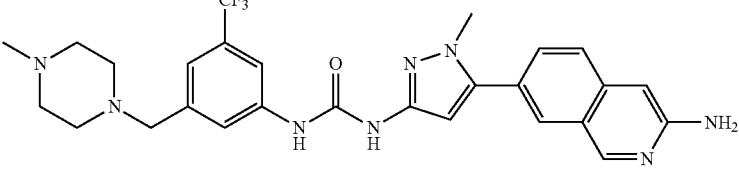 |
| 93 | 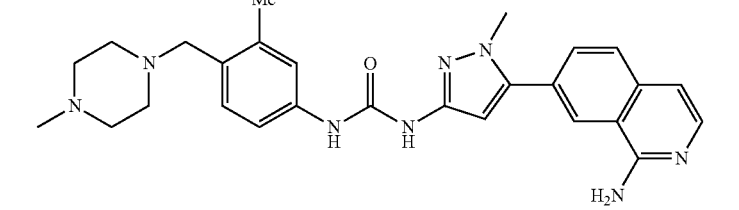 |

TABLE 4-continued

| Compound No. | Structure |
|---|---|
| 94 | *(chemical structure)* |
| 95 | *(chemical structure)* |
| 96 | *(chemical structure)* |
| 97 | *(chemical structure)* |
| 98 | *(chemical structure)* |
| 99 | *(chemical structure)* |

More specifically, the inventive compound can be any of the specific examples shown herein as exemplary compounds of the invention.

Methods of Use

XBP1 is believed to sustain dendritic cell immunosuppressive activity within the tumor microenvironment by directly upregulating enzymes involved in triglyceride biosynthesis (Cubillos-Ruiz et al., Cell 161(7): 1527-38 (2015)). XBP1, also known as X-box binding protein 1, is a transcription factor that regulates the expression of genes involved in the proper functioning of the immune system and in the cellular stress response, it is believed that IRE1α-mediated XBP1 activation is fueled by the induction of reactive oxygen species and subsequent formation of peroxidized lipids.

The most conserved arm of the endoplasmic reticulum (ER) stress response is the dual enzyme, IRE1α. Activated during periods of ER stress, the IRE1α in endoribonuclease domain excises a short nucleotide fragment from Xbp1 mRNA to generate the functional transcription factor, XBP1.

This potent, multitasking protein promotes cell survival by upregulating expression of a broad range of critical genes involved in protein folding and quality control. XBP1 drives the pathogenesis of triple negative breast cancer (TNBC) by promoting tumor cell survival and metastatic capacity under hypoxic conditions. Silencing of XBP1 in TNBC leads to suppression of tumor initiation, progression, and recurrence.

Unexpectedly, the inventors have identified a second mechanism by which XBP1 promotes tumor progression: by confounding the development of protective antitumor immunity in the ovarian cancer tumor microenvironment. Without XBP1, tumor resident dendritic cells failed to accumulate intracellular lipids, which normally disrupt effective antigen cross-presentation. This pathological lipid accumulation is fundamentally driven by reactive oxygen species-mediated lipid peroxidation, which directly destabilizes protein-folding chaperones within the endoplasmic reticulum to induce a state of ER stress and XBP1 activation. Additionally, it is believed that IRE1α-mediated XBP1 signaling is also critical for myeloid cell production of immunosuppressive prostaglandins such as prostaglandin E2 (PGE2).

Novel small-molecule IRE1α inhibitors with the ability to induce two parallel and mutually reinforcing anti-tumor mechanisms, namely the direct inhibition of tumor growth and the simultaneous induction of robust anti-tumor immunity are highly desirable, as no effective, targeted therapies currently exist for either TNBC or ovarian cancer. The compositions and methods described herein are novel IRE1α kinase inhibitors that exhibit immune-modulatory properties. No currently existing compounds possess activity in the presence of human or mouse ovarian cancer ascites, a critical requirement for IRE1α inhibitor usage clinically.

Novel direct and indirect small molecule IRE1α inhibitors can prevent lipid accumulation in myeloid cells exposed to ovarian cancer-derived ascites supernatants. Furthermore, the identified direct IRE1α inhibitors have unique chemical structures compared to currently available compounds, and therefore can have unique binding mechanisms, inhibitory activity, and off-target effects. Additionally, the inventors have demonstrated that these compounds block myeloid cell immunosuppression mediated by tumor-associated factors. The invention also includes novel uses for vitamin E and hydralazine derivatives, which indirectly prevent IRE1α activation and thereby suppress cancer cell-induced lipid accumulation in myeloid dendritic cells.

The IRE1α-XBP1 pathway is therefore involved in a variety of pathological conditions, including neurodegenerative diseases, inflammation, metabolic disorders, liver dysfunction, brain ischemia, heart ischemia, autoimmune diseases, and cancer. Hence, modulation of this pathway provides therapeutic methods useful for treatment of such diseases. The identified small molecule compounds can, for example, be employed as therapeutic compounds that enhance dendritic cell and T cell anti-tumor activity in mammals. For example, the compounds disclosed herein can be used to treat murine and human ovarian cancers.

Hence, a method is described herein that includes administering any of the compounds or the composition described herein. The mammal can be in need of administration of the composition. For example, the mammal can have cancer, a neurodegenerative disease, inflammation, a metabolic disorder, liver dysfunction, brain ischemia, heart ischemia, or an autoimmune disease. In some cases, the mammal has triple negative breast cancer or ovarian cancer.

Compositions and Combination Treatments

The IRE1α inhibitor compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another IRE1α to inhibitor or another type of therapeutic agent, or both. For example, the compositions and methods described herein can include one or more agents such as vitamin E, an antioxidant, and/or hydralazine. Such agents can sequester lipid peroxidation byproducts, and can be effective treatments for controlling ER stress responses and sustained IRE1α/XBP1 signaling in tumor-associated dendritic cells exposed, for example, to ovarian cancer-derived ascites.

As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g. as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include one or more compounds of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate err glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention which inhibits the activity of the IRE1α to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is nonvolatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention which inhibits the enzymatic activity of the focal adhesion kinase, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tableting techniques can contain:

| Core: | Active compound (as free compound or salt, thereof) | 250 mg |
|---|---|---|
| | Colloidal silicon dioxide (Aerosil) ® | 1.5 mg |
| | Cellulose, microcryst. (Avicel) ® | 70 mg |
| | Modified cellulose gum (Ac-Di-Sol) ® | 7.5 mg |
| | Magnesium stearate | Ad. |
| Coating: | HPMC approx. | 9 mg |
| | *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a human in need of such treatment, prevention, elimination, alleviation or amelioration of a malcondition that is mediated through the action of IRE1α, for example, cancer, neurodegenerative diseases, inflammation, metabolic disorders, liver dysfunction, brain ischemia, or heart ischemia.

The pharmaceutical compositions and compounds of the present invention can generally be administered in the form of a dosage unit (e.g. tablet, capsule, etc.) in an amount from about 1 ng/kg of body weight to about 0.5 g/kg of body weight, or from about 1 μ/kg of body weight to about 500 mg/kg of body weight, or from about 10 μ/kg of body weight to about 250 mg/kg of body weight, most preferably from about 20 μ/kg of body weight to about 100 mg/kg of body weight. Those skilled in the art will recognize that the particular quantity of pharmaceutical composition and/or compounds of the present invention administered to an individual will depend upon a number of factors including, without limitation, the biological effect desired, the condition of the individual and the individual's tolerance for the compound.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge. IRE1α inhibitor bioactivity of the compounds of the invention can be determined by use of an in vitro assay system which measures the activity of IRE1α, which can be expressed as $EC_{50}$ or $IC_{50}$ values, as are well known in the art inhibitors of the invention can be determined by the method described in the Examples.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 μg to about 1250 mg, preferably from about 250 μg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g., specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other IRE1α inhibitors and/or ii) one or more other types of protein kinase inhibitors and/or one or more other types of therapeutic agents which can be administered orally in the same dosage form, in a separate oral dosage form (e.g., sequentially or non-sequentially) or by injection together or separately (e.g., sequentially or non-sequentially).

Accordingly, in another embodiment the invention provides combinations, comprising:

a) a compound of the invention as described herein; and
b) one or more compounds comprising:
  i) other compounds of the present invention,
  ii) other agents or medicaments adapted for treatment of a disease or malcondition for which inhibition of IRE1α is medically indicated, for example, vitamin E, an antioxidant, hydralazine, or any combination thereof. Such compounds, agents or medicaments can be medically indicated for treatment of cancers such as TNBC or ovarian cancer, neurodegenerative diseases, inflammation, metabolic disorders, liver dysfunction, autoimmune diseases, brain ischemia, or heart ischemia.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the *Physicians' Desk Reference*, incorporated herein by reference.

The Examples illustrate some of experimental work performed in the development of the invention.

Example 1: Vitamin E and Hydrazine Suppress Lipid Accumulation in Myeloid Dendritic Cells Consistently, both vitamin E and hydralazine suppressed pathological intracellular lipid accumulation in myeloid dendritic cells exposed to ovarian cancer ascites supernatants (FIG. 1). Based on the strong evidence linking aberrant lipid accumulation myeloid cell immunosuppression, these agents can be used to restore the function of antigen presenting cells in the tumor microenvironment.

Example 2: FRET Assay

In addition to the indirect inhibitors vitamin E and hydralazine, the compositions and methods described herein can include one or more direct, small molecule IRE1α inhibitors.

IRE1α is a dual enzyme, containing a kinase and endoribonuclease domain. Phosphorylation of the kinase domain during times of ER stress leads to activation of the endoribonuclease domain and subsequent Xbp1 splicing, indicating that small molecules designed to block either the kinase domain or the endoribonuclease domain are feasible inhibitory strategies.

Figure 2A:
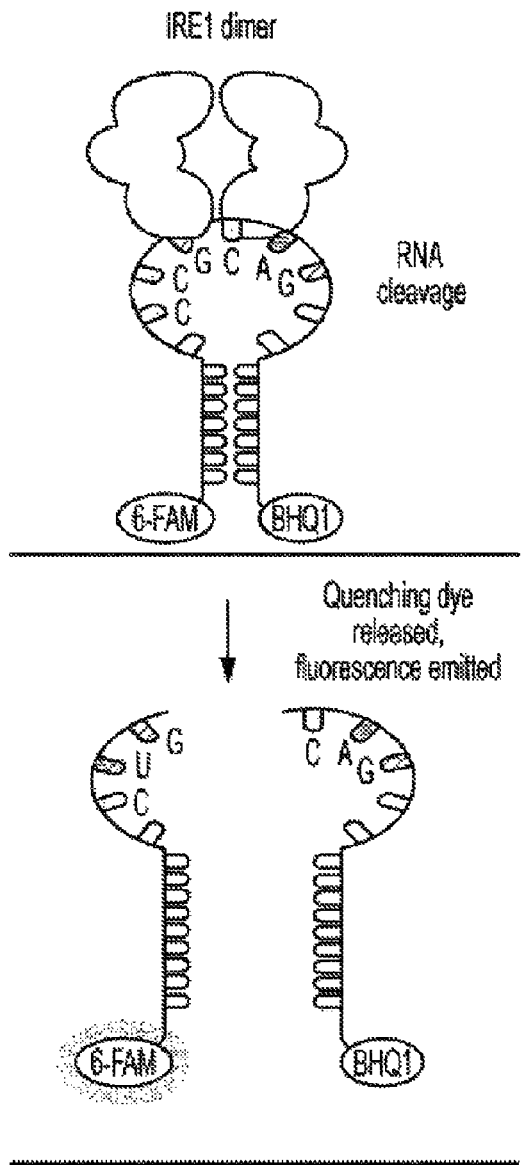
FIG. 2A is a cartoon of a cleavable RNA probe and IRE1α-dependent hairpin cleavage site.
Figure 2B:
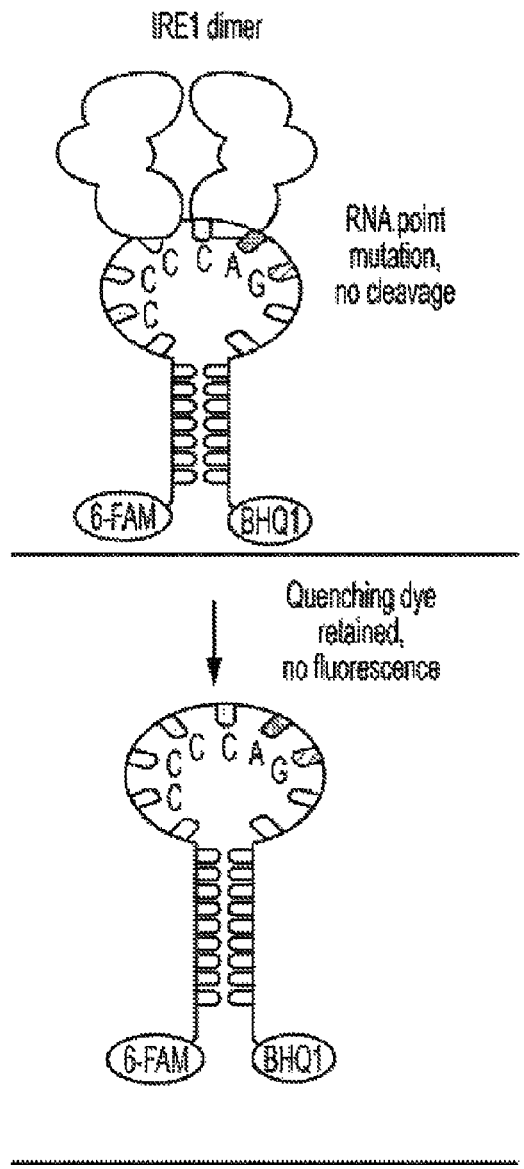
FIG. 2B is a cartoon of a point mutation (G→C) in the hairpin that abrogates IRE1α activity against RNA probe, controlling for contamination by non-specific RNAses.

To evaluate potential small molecule IRE1 inhibitors, a Förster resonance energy transfer (FRET)-based small molecule IRE1 screening system was used. In brief, a small XBP1-mimetic RNA hairpin containing sequence features required for IRE1α-mediated splicing has been synthesized with the fluorophore 6FAM attached to the 5' end and the quenching dye Black Hole Quencher 1 (BHQ1) attached to the 3' end. When the hairpin is intact, 6FAM fluorescence is completely absorbed by BHQ1; however, IRE1α-mediated cleavage of the RNA hairpin leads to an increase in the fluorescence signal. The inventors also incorporated a point mutant version of this same RNA hairpin that is resistant to IRE1α-mediated cleavage to control for non-specific RNAse contamination (FIG. 2).

Example 3: Potent IRE1α Inhibitors Identified by FRET Assay

Figure 3:
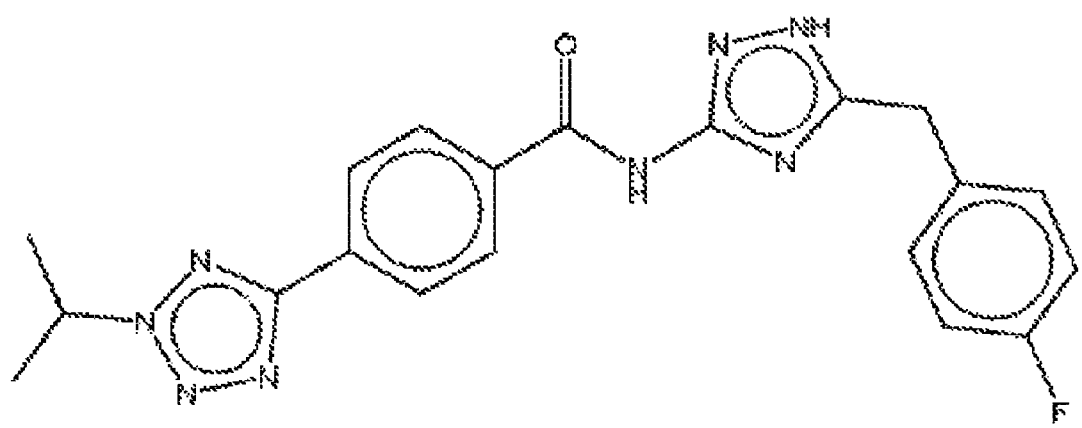
FIG. 3 is the structure of an IRE1α inhibitor identified by computational screening and confirmed by human IRE1α FRET assay (commercially available from InterBioScreen).

Approximately 170 compounds were obtained and evaluated using the FRET assay, and at least one active compound was identified from this screen (1050: 26 µM, FIG. 3). Compound activity was evaluated at the biotechnology company Cyclofluidic guided entirely by the inventors.

Example 4: Computational Screening

After establishing the FRET system, computational models of IRE1α based on published crystal structures were used to dock over 7 million compounds commercially available from the company eMolecules. Docking was performed using the Schrodinger software suite.

The cytoplasmic domain of human IRE1α (approximately residues 465-977) has been crystallized five separate times (PDBs 4PL3, 4U6R, 4PL4, 4PL5, and 3P23) in different states of phosphorylation and activation, as well as with both endoribonuclease inhibitors and kinase inhibitors (Sanches et al., Nature Communications 5:4202 (2014); Harrington et al., ACS Med Chem Letters 6:68-72 (2015); Ali et al., The EMBO J 30:894-905 (2011)). These studies and others (see, e.g., Wang et al., Nature Chem Biol 8:982-9 (2012)) provide substantial evidence that IRE1α kinase inhibitors can either inhibit or activate the IRE1α endoribonuclease domain depending on their binding mode.

Type I kinase inhibitors that lock the IRE1α kinase domain into a "DFG-out" conformation block endoribonuclease activity, while inhibitors that lock the kinase domain into a "DFG-in" conformation trigger mRNA splicing despite abrogating autophosphorylation.

All known endoribonuclease inhibitors bind to a shallow pocket in a highly solvent exposed manner at the IRE1α C-terminus, and make too few key binding contacts to effectively model computationally.

At the time this project was initiated, the only kinase inhibitor co-crystallized with IRE1α enforced a Type I. DFG-in configuration (PDB 4U6R). To generate a model of IRE1α in the target Type II, DFG-out configuration, the inventors computationally grafted the DFG loop from the crystal structure of the SRC kinase bound to the type II inhibitor 1-(4-(4-Amino-1-isopropyl-1H-pyrazolo[3,4-d]pyrimidin-3-yl)phenyl)-3-(3-(trifluoromethyl)phenyl)urea onto the 4U6R IRE1 crystal structure, as this compound also inhibits the IRE1α kinase and endoribonuclease domains. After grafting the SRC DFG-loop onto the IRE1α crystal structure, the SRC inhibitor was docked into the hybrid model for quality control.

The SRC inhibitor exhibited a good docking score using unconstrained rigid receptor docking, as its urea group made hydrogen bonds with both a serine residue N-terminal to the DFG loop and a lysine-aspartate salt bridge in the kinase active site. With the initial model validated, the set of all compounds commercially available from the company eMolecules (over 7 million in sum) was used as the screening collection. From the full list of 7 million compounds, only urea and amide-containing structures were computationally docked (~800,000 compounds), as these motifs form key hydrogen bond interactions with kinase DFG loops. Top scoring compounds were clustered by structural similarity and filtered for those with desirable properties, and the top scoring compounds from each of 49 clusters were ordered and tested by FRET assay.

Initial results indicated that one of the 49 compounds exhibited some activity against IRE1. The structure-activity relationships of an additional 62 compounds were examined. However, secondary screening after FRET assay optimization, performed at the CRO Cyclofluidic, revealed that none of these 111 compounds exerted any activity. Cyclofluidic had published a small set of approximately 50 compounds (5) from their internal work on derivatives of the BCR-ABL kinase inhibitor Ponatinib, and the inventors also screened these published compounds for IRE1α inhibitory activity.

While optimizing the first compound series, new crystal structures of IRE1α in complex with Type II, DFG-out-inducing kinase inhibitors became available (Concha et al., Molecular Pharmacol 88:1011-2 (2015)), which was used to develop a second model of IRE1α.

First, the ponatinib-like compounds were docked into this new model, allowing some structural flexibility, to control for model quality. Subsequently, a second computational screen was performed with the updated model, and compounds for follow up were selected as follows:
1. Docked into the ponatinib-like compound induced structure.
2. H-bond with hinge NH
3. Strained compounds removed
4. Any compound with similarity to any of the known compounds tested thus far removed
5. Clustering
6. Selecting the highest docking score per cluster The top 63 compounds based on this strategy were then tested, and only one compound showed weak activity by FRET assay (FIG. 3).

Example 5: Design of Additional Compounds

New small molecule compounds were designed to inhibit the human IRE1α kinase domain. Multiple variants of the original compound series were designed and ranked by computational docking score using the software LiveDesign. High scoring compounds were synthesized and evaluated biochemically by the IRE1α FRET assay.

Example 6: In Vitro FRET Assay Protocol

In vitro FRET assay was performed to evaluate the ability of select compounds to inhibit IRE1, the results of which are summarized in the following table.

To perform the in vitro FRET assay, 1× complete assay buffer (CAB; 1M DTT, 50 mM sodium citrate pH 7.15, 1 mM magnesium acetate, 0.02% Tween 20) was used to dilute SignalChem IRE1α in protein to a final concentration of 2 nM. Selected compounds were serially diluted with DMSO in a non-binding black 384-well plate for a total of 15 µl in each well. 2 µl of the serially diluted compound or DMSO control were then added to new wells containing 98 µl of 1×CAB, for a total volume of 100 µl, 10 µl of which were then transferred to wells of a new plate. 5 µl of the diluted IRE1α was then added to each well. 5 µl of a 400 mM XBP1 RNA probe was then added to each well. Fluorescence was then read over 30 minutes in kinetic mode (485/515 nm). Two RNA probes were used, XBP1 wildtype (CAUGUCCGCAGCACAUG; SEQ ID NO: 1) which is able to be spliced by active IRE1α or XBP1 mutant (CAUGUCCCCAGCACAUG; SEQ ID NO: 2) which is unable to be spliced. Each probe contained a 5' 6-FAM modification and a 3' IOWA Black FQ modification.

A second FRET assay was performed to assess ATP-mediated inhibition. In this case, compounds and IRE1α were prepared and combined as discussed above, with the addition of ATP up to 1 mM final concentration. This mixture was incubated at room temperature for 60 minutes and then 5 µl of 400 nM XBP1 wildtype or mutant RNA probe was added. Plates were then read over 30 minutes in kinetic mode (485/515 nm).

| Compound Ref. No. | Mean EC$_{50}$ (nM) |
|---|---|
| 76 | C |
| 75 | A |
| 74 | A |
| 21 | C |
| 73 | A |
| 52 | A |
| 51; Formic Acid | B |
| 50; HCl | B |
| 72 | C |
| 49; TFA | D |
| 48; TFA | B |
| 71; TFA | B |
| 20 | D |
| 19 | D |
| 47 | D |
| 70 | D |
| 69 | D |
| 68 | D |
| 46; TFA | A |
| 45; TFA | B |
| 67; TFA | D |
| 66; TFA | D |
| 65 | D |
| 64 | D |
| 63 | D |
| 62 | D |
| 44 | B |
| 43 | D |
| 42 | D |
| 41 | D |
| 40 | D |
| 39 | D |
| 38 | D |
| 37 | A |
| 36 | A |
| 35 | A |
| 61 | D |
| 34; TFA | B |
| 33; TFA | B |
| 32; TFA | D |
| 31; TFA | B |
| 18; TFA | D |
| 17; TFA | D |
| 16; TFA | A |
| 15; HCl | D |
| 14 | C |
| 13 | D |
| 60 | B |
| 59 | B |
| 58; HCl | D |
| 57 | B |
| 56 | D |
| 30 | D |
| 30 | A |
| 12 | B |
| 11 | B |
| 10 | B |
| 9 | A |
| 8 | A |
| 29 | A |
| 28 | A |
| 27 | A |
| 26; TFA | A |
| 55 | B |
| 7 | B |
| 54 | A |
| 53 | D |
| 6 | D |
| 25 | B |
| 24; TFA | A |
| 5 | D |
| 4 | D |
| 3 | D |
| 23 | B |
| 2 | B |
| 22 | A |
| 1 | A |

Note:
Biochemical assay Mean EC$_{50}$ data are designated within the following ranges:
A: ≤5000 nM
B: >5000 nM to ≤50000 nM
C: >50000 nM to ≤100000 nM
D: >100000 nM

REFERENCES

1. Wang, L., et al., *Divergent allosteric control of the IRE1alpha endoribonuclease using kinase inhibitors.* Nat Chem Biol, 2012. 8(12): p. 982-9.
2. Harrington, P. E., et al., *Unfolded Protein Response in Cancer: IRE1alpha Inhibition by Selective Kinase Ligands Does Not Impair Tumor Cell Viability.* ACS Med Chem Lett, 2015. 6(1): p. 68-72.
3. Concha, N. O., et al., *Long-Range Inhibitor-Induced Conformational Regulation of Human IRE1alpha Endoribonuclease Activity.* Mol Pharmacol, 2015. 88(6): p. 1011-23.
4. Mendez, A. S., et al., *Endoplasmic reticulum stress-independent activation of unfolded protein response kinases by a small molecule ATP-mimic.* Elife, 2015. 4.
5. Cross, B. C., et al., *The molecular basis for selective inhibition of unconventional mRNA splicing by an IRE1-binding small molecule.* Proc Natl Acad Sci USA, 2012. 109(15): p. E869-78.
6. Tang, C. H., et al., *Inhibition of ER stress-associated IRE-1/XBP-1 pathway reduces leukemic cell survival.* J Clin Invest, 2014. 124(6): p. 2585-98.
7. Volkmann, K., et al., *Potent and selective inhibitors of the inositol-requiring enzyme 1 endoribonuclease.* J Biol Chem, 2011. 286(14): p. 12743-55.
8. Papandreou, I., et al., *Identification of an Ire1alpha endonuclease specific inhibitor with cytotoxic activity against human multiple myeloma.* Blood, 2011. 117(4): p. 1311-4.
9. Mimura, N., et al., *Blockade of XBP1 splicing by inhibition of IRE1alpha is a promising therapeutic option in multiple myeloma.* Blood, 2012. 119(24): p. 5772-81.
10. Cubillos-Ruiz, J. R., et al., *ER Stress Sensor XBP1 Controls Anti-tumor Immunity by Disrupting Dendritic Cell Homeostasis.* Cell, 2015. 161(7): p. 1527-38.
11. Desai, B., et al., *Rapid discovery of a novel series of Abl kinase inhibitors by application of an integrated microfluidic synthesis and screening platform.* J Med Chem, 2013. 56(7): p. 3033-47.
12. Sanches M, Duffy N M, Talukdar M, Thevakumaran N, Chiovitti D, Canny M D, et al. *Structure and mechanism of action of the hydroxy-aryl-aldehyde class of IRE1 endoribonuclease inhibitors.* Nature communications. 2014; 5:4202.
13. Harrington P E, Biswas K, Malwitz D, Tasker A S, Mohr C, Andrews K L, et al. *Unfolded Protein Response in Cancer: IRE1alpha Inhibition by Selective Kinase Ligands Does Not Impair Tumor Cell Viability.* ACS medicinal chemistry letters. 2015; 6:68-72.
14. Ali M M, Bagratuni T, Davenport E L, Nowak P R, Silva-Santisteban M C, Hardcastle A, et al. *Structure of* the Ire1 autophosphorylation complex and implications for the unfolded protein response. The EMBO journal. 2011; 30:894-905.
15. Wang L, Perera B G, Hari S B, Bhhatarai B, Backes B J, Seeliger M A, et al. *Divergent allosteric control of the IRE1alpha endoribonuclease using kinase inhibitors.* Nature chemical biology. 2012; 8:982-9.
16. Desai B, Dixon K, Farrant E, Feng Q, Gibson K R, van Hoorn W P, et al. *Rapid discovery of a novel series of Abl kinase inhibitors by application of an integrated microfluidic synthesis and screening platform.* Journal of medicinal chemistry. 2013; 56:3033-47.
17. Concha N O, Smallwood A, Bonnette W, Totoritis R, Zhang G, Federowicz K, et al. *Long-Range inhibitor-Induced Conformational Regulation of Human IRE1alpha Endoribonuclease Activity.* Molecular pharmacology. 2015; 88:1011-23.

All patents and publications referenced herein are hereby specifically incorporated by reference to the same extent as if it had been incorporated by reference in its entirety individually or set forth herein in its entirety. Applicants reserve the right to physically incorporate into this specification any and all materials and information from any such cited patents or publications.

Additional Embodiments

The following exemplary embodiments are provided, the numbering of which is not to be construed as designating levels of importance:

Embodiment 1 provides a compound of formula I:

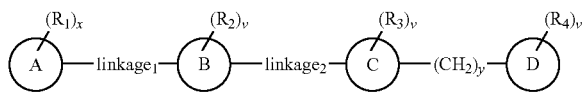

wherein:
A and B are separately each a heterocyclyl ring or a phenyl group, where the A ring has x $R_1$ substituents;
C is phenyl or pyridinyl;
D is heterocyclyl ring;
linkage$_1$ is a single bond between A and B;
linkage$_2$ is a $C_1$-$C_3$ alkylamido, amidoalkyl, amino, urea, alkylurea, or ureaalkyl with a first and second terminal atom;
y is an integer of 0-3, and when y is 0, the linkage between the rings is a single bond;
x is an integer of 0-4;
v is an integer of 0-2;
$R_1$ substituents on the A ring are selected from amino, optionally substituted $C_1$-$C_4$ alkyl, optionally substituted ether, optionally substituted $C_1$-$C_4$ alkoxy, oxy, hydroxy, —NH—SO$_2$-phenyl-(R$_5$), and cyano;
$R_2$ substituents on the B ring are selected from amino, and optionally substituted $C_1$-$C_4$ alkyl;
$R_3$ substituents on the C ring are selected from halo, CF$_3$, optionally substituted $C_1$-$C_4$ alkyl, and optionally substituted heteroaryl; and
$R_4$ substituents on the D ring are selected from optionally substituted $C_1$-$C_4$ alkyl, optionally substituted $C_1$-$C_4$ alkoxy, (optionally substituted $C_1$-$C_3$ alkylene)-OH, hydroxy, optionally substituted aryl, optionally substituted benzyl, and optionally substituted benzaldehyde;

$R_5$ is halo; or a pharmaceutically acceptable salt thereof.

Embodiment 2 provides the compound of embodiment 1, where the A ring is heteroaromatic.

Embodiment 3 provides a compound of any one of embodiments) or 2, where the A ring is a fusion of two rings.

Embodiment 4 provides a compound of any one of embodiments 1-3, where the A ring is indazole, imadazopyridine, imadazopyrazine, imadazopyridazine, pyrrolopyridine, hexahydrothienopyrimidine, imidazole, pyrazole, pyrazine, pyridine, pyrimidine, phenylpyrimidinamine, quinolinyl, isoquinolinyl, tetrahydroquinolinyl, and quinazolinyl.

Embodiment 5 provides a compound of any one of embodiments 1-4, where the A ring is selected from:

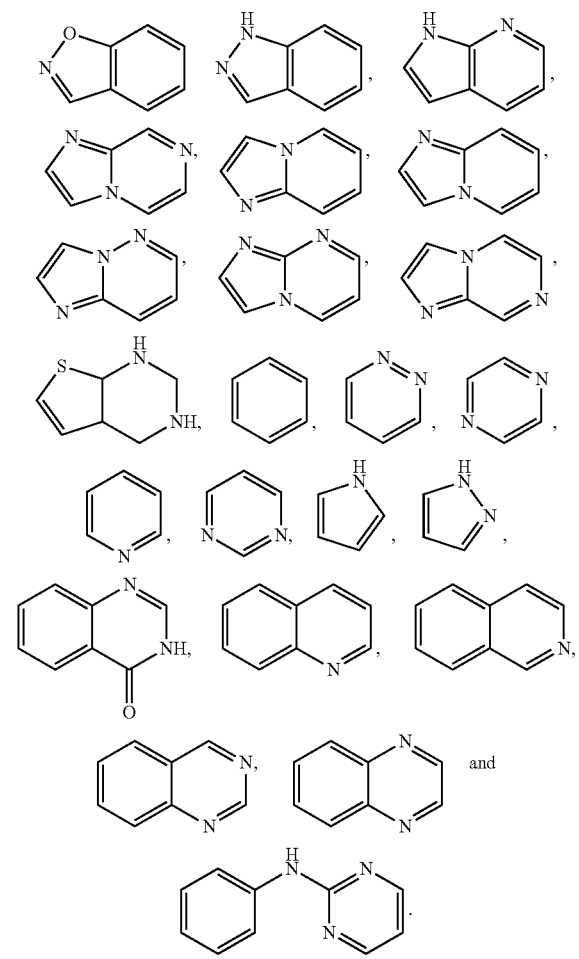

Embodiment 6 provides a compound of any one of embodiments 1-5, where the B ring is a single, non-fused ring.

Embodiment 7 provides a compound of embodiment 6, where the B ring is B ring is pyrazolyl, imidazolyl, or triazolyl.

Embodiment 8 provides a compound of any one of embodiments 1-5, where the B ring is a fusion of two rings.

Embodiment 9 provides a compound of any one of embodiments 1-8, where the B ring is selected from:

Embodiment 10 provides a compound of any one of embodiments 1-9, wherein the C ring is phenyl.

Embodiment 11 provides a compound of any one of embodiments 1-10, wherein the linkage₂ is selected from:

wherein a hydrogen atom on Ring B replaced by the first terminal atom of linkage₂ and a hydrogen atom on Ring C is replaced by the second terminal atom of linkage₂.

Embodiment 12 provides a compound of any one of embodiments 1-11, wherein the D ring is a heterocyclyl ring containing at least one N atom.

Embodiment 13 provides a compound of embodiment 12, wherein the D ring is piperidinyl, piperazinyl, or morpholinyl.

Embodiment 14 provides a compound of any one of embodiments 1-11, wherein D ring is selected from Embodiment 15 provides a compound of any one of embodiments 1-14, where the $R_1$ substituents on the A ring are selected from amino and $C_1$-$C_3$ alkyl.

Embodiment 16 provides a compound of any one of embodiments 1-15, where the $R_1$ substituents on the A ring are selected from —$NH_2$ and $CH_3$.

Embodiment 17 provides a compound of any one of embodiments 1-14, with x=0.

Embodiment 18 provides a compound of any one of embodiments 1-16, with x=1.

Embodiment 19 provides a compound of any one of embodiments 1-16, with x=2.

Embodiment 20 provides a compound of any one of embodiments 1-19, with x=0, 1 or 2 when the A ring is a fusion of two rings.

Embodiment 21 provides a compound of any one of embodiments 1-16, with x=1 or 2 when the A ring is a single, nonfused ring.

Embodiment 22 provides a compound of any one of embodiments 1-21, wherein the $R_3$ substituent on the C ring is $CF_3$.

Embodiment 23 provides a compound of any one of embodiments 1-22, wherein the $R_4$ substituents on the D ring are selected from $CH_3$, $CH_3CHCH_3$, $CH_3CH(CH_2)CH_3$, and $CH_3CH_2CH_3OH$.

Embodiment 24 provides a compound of formula Ia:

Ia wherein,
$A_1$ is N, CH, or $CR_1$; $A_2$ is N, CH, or $CR_1$; $A_3$ is N, CH, or $CR_1$; $A_4$ is N, CH, or $CR_1$; $A_5$ is N, CH, or $CR_1$; $A_6$ is N, CH, or $CR_1$; $A_7$ is N CH, or $CR_1$;

v is an integer of 0-2;

Each $R_1$ is $NH_2$ or OH; provided that the number of $R_1$ on the A ring does not exceed B is selected from:

each $R_2$ is independently selected from H and optionally substituted $C_1$-$C_4$ alkyl;

$X_1$ and $X_2$ are each independently $CH_2$ or NH; with the provision that $X_1$ and $X_2$ are not each $CH_2$;

$R_3$ is selected from H, halo, $CF_3$, optionally substituted $C_1$-$C_4$ alkyl, and optionally substituted heteroaryl;

D is heterocyclyl ring containing at least one N atom; and each $R_4$ is selected from H, optionally substituted $C_1$-$C_4$ alkyl, optionally substituted $C_1$-$C_4$ alkoxy, (optionally substituted $C_1$-$C_4$ alkylene)-OH, hydroxy, optionally substituted aryl, and optionally substituted benzyl; or a pharmaceutically acceptable salt thereof.

Embodiment 25 provides a compound selected from any of the compounds in Tables 1-4, the Examples, or pharmaceutically acceptable salts thereof.

Embodiment 26 provides a compound of any one of embodiments 1-25, pharmaceutically acceptable salts thereof, or any combination of such compounds or salts.

Embodiment 27 provides a compound of embodiment 26, further comprising vitamin E, an antioxidant, hydralazine, or any combination thereof.

Embodiment 28 provides a method comprising administering the composition of any one of embodiments 26 or 27 to a mammal.

Embodiment 29 provides a method of embodiment 28, wherein the mammal is in need of administration of the composition.

Embodiment 29 provides a method of any one of embodiments 28 or 29, wherein the mammal has cancer, a neurodegenerative disease, inflammation, a metabolic disorder, liver dysfunction, an autoimmune disease, brain ischemia, or heart ischemia.

Embodiment 29 provides a method of any one of embodiments 28-30, wherein the mammal has triple negative breast cancer or ovarian cancer.

Embodiment 30 provides a compound of any one of embodiments 1-25 for use in treating cancer.

Embodiment 31 provides a use of a compound of any one of embodiments 1-25 in treating cancer.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "a catalyst" or "a ligand" includes a plurality of such compounds, catalysts or ligands, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of formula Ia:

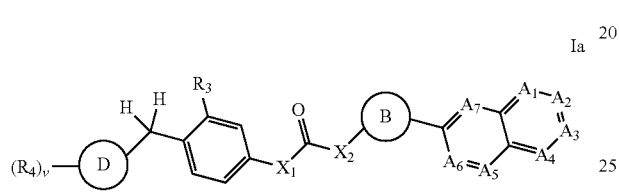

wherein,
- $A_1$ is N, CH, or $CR_1$; $A_2$ is N, CH, or $CR_1$; $A_3$ is N, CH, or $CR_1$; $A_4$ is N, CH, or $CR_1$; $A_5$ is N, CH, or $CR_1$; $A_6$ is N, CH, or $CR_1$; $A_7$ is N, CH, or $CR_1$;
- v is an integer of 0-2;
- each $R_1$ is $NH_2$ or OH; provided that the number of $R_1$ on the A ring does not exceed 4;
- B is selected from:

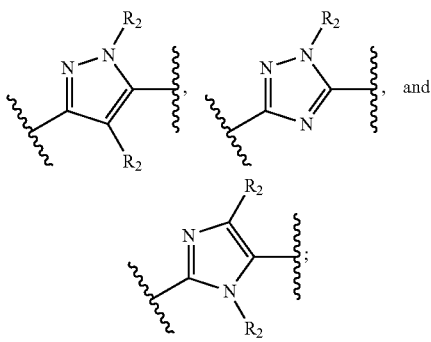

each $R_2$ is independently selected from H and optionally substituted $C_1$-$C_4$ alkyl;
$X_1$ and $X_2$ are each independently $CH_2$ or NH; with the provision that $X_1$ and $X_2$ are not each $CH_2$;
$R_3$ is selected from H, halo, $CF_3$, optionally substituted $C_1$-$C_4$ alkyl, and optionally substituted heteroaryl;
D is a heterocyclyl ring containing at least one N atom; and
each $R_4$ is selected from H, optionally substituted $C_1$-$C_4$ alkyl, optionally substituted $C_1$-$C_4$ alkoxy, (optionally substituted $C_1$-$C_4$ alkylene)-OH, hydroxy, optionally substituted aryl, and optionally substituted benzyl; or a pharmaceutically acceptable salt thereof.

2. The compound of claim 1, wherein $A_1$ is CH or $CR_1$; $A_2$ is N; $A_3$ is CH or $CR_1$; $A_4$ is N, CH, or $CR_1$; $A_5$ is CH or $CR_1$; $A_6$ is CH or $CR_1$; and $A_7$ is CH or $CR_1$.

3. The compound of claim 1, wherein B is

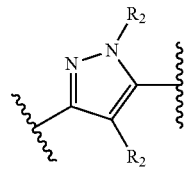

and each $R_2$ is independently H or methyl.

4. The compound of claim 1, wherein $R_3$ is selected from H, halo, and $CF_3$.

5. The compound of claim 1, wherein D is selected from:

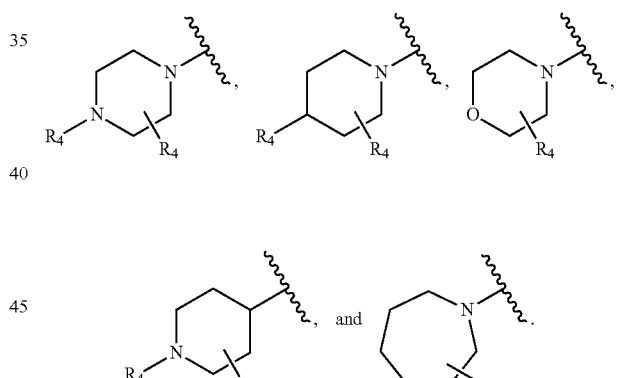

6. The compound of claim 1, wherein v is 1; and $R_4$ is selected from H, optionally substituted $C_1$-$C_4$ alkyl, (optionally substituted $C_1$-$C_4$ alkylene)-OH, hydroxy, optionally substituted aryl, and optionally substituted benzyl.

7. A composition comprising a carrier and a compound of claim 1.

8. A method for treating or reducing cancer, comprising: administering to a subject in need thereof, the compound of claim 1.

9. A method for clearing cancer cells, comprising: administering to a subject in need thereof, the compound of claim 1.

10. The compound of claim 1, wherein the compound is
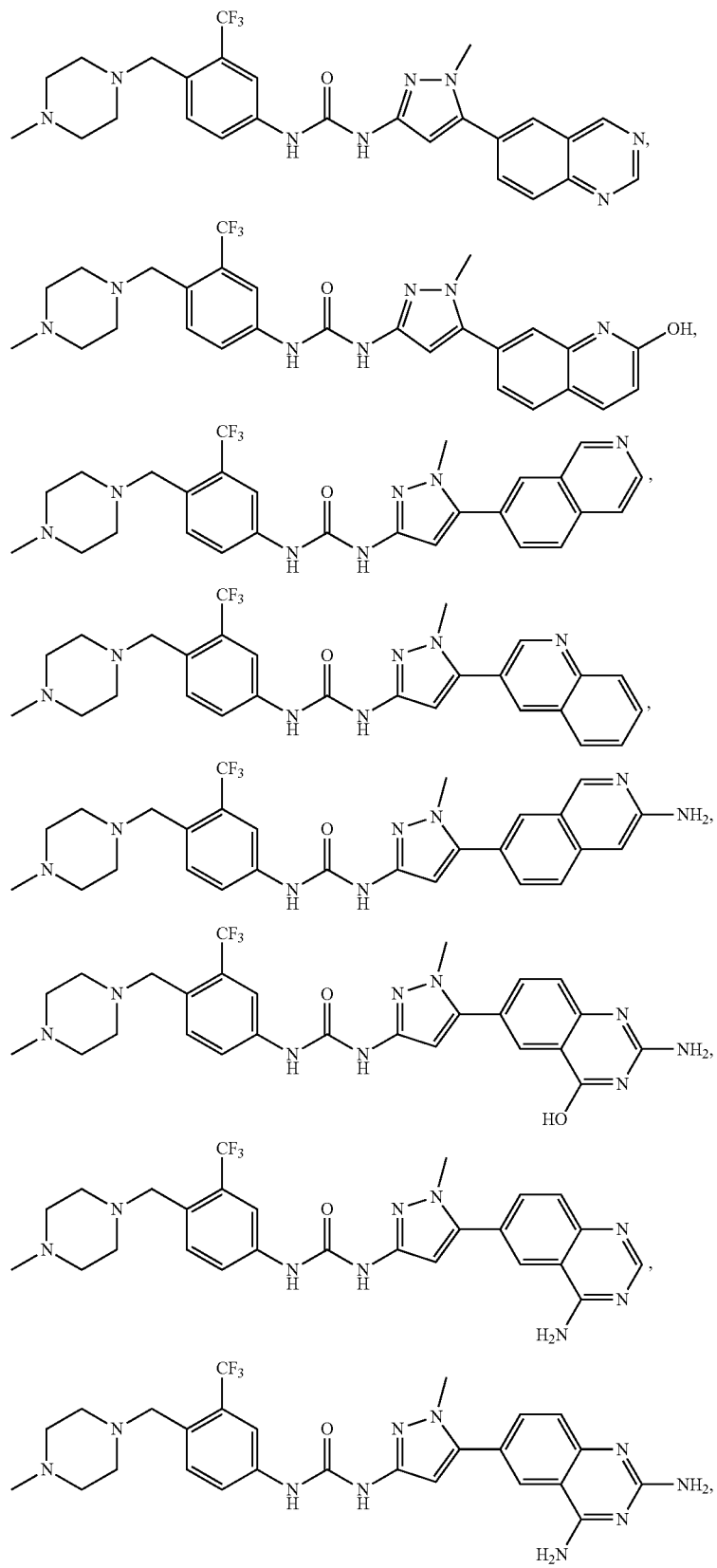

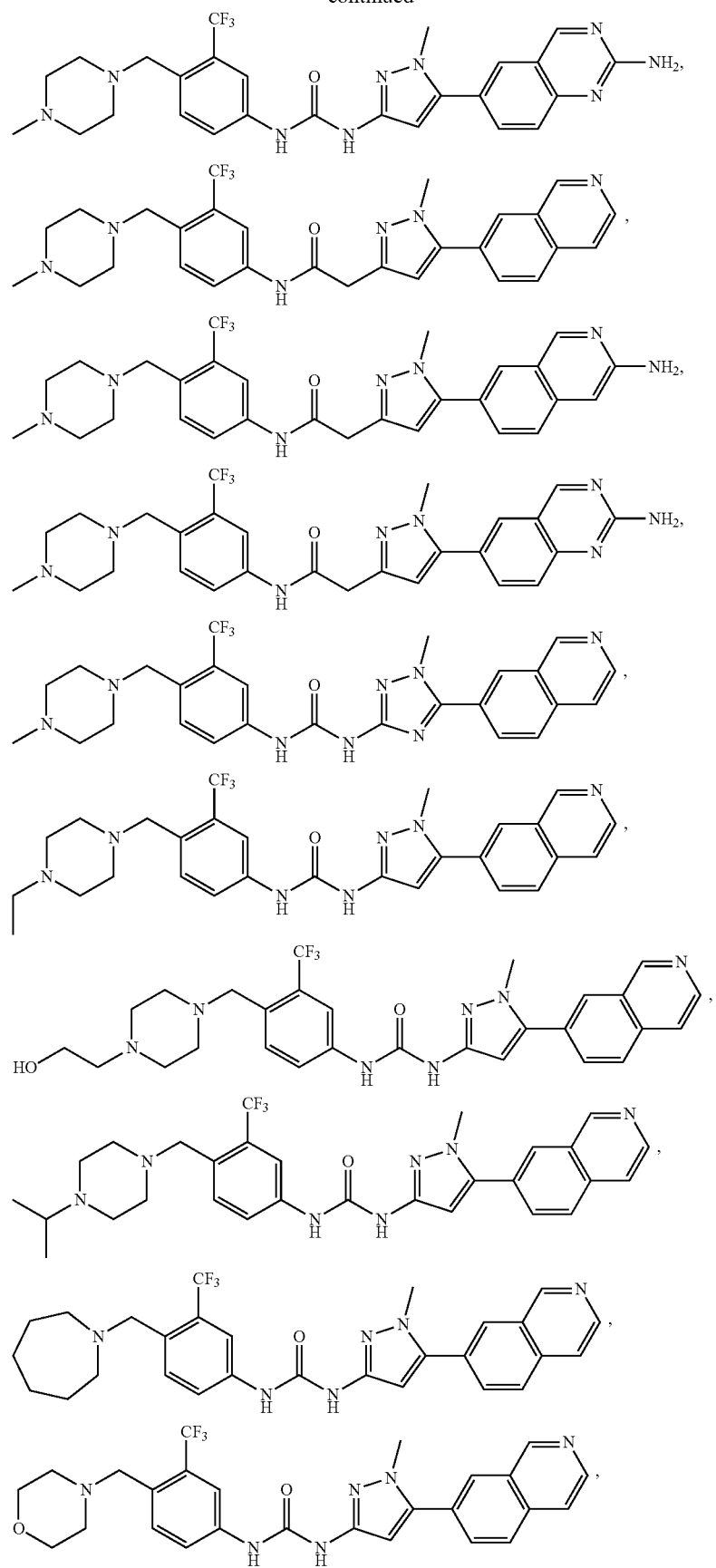

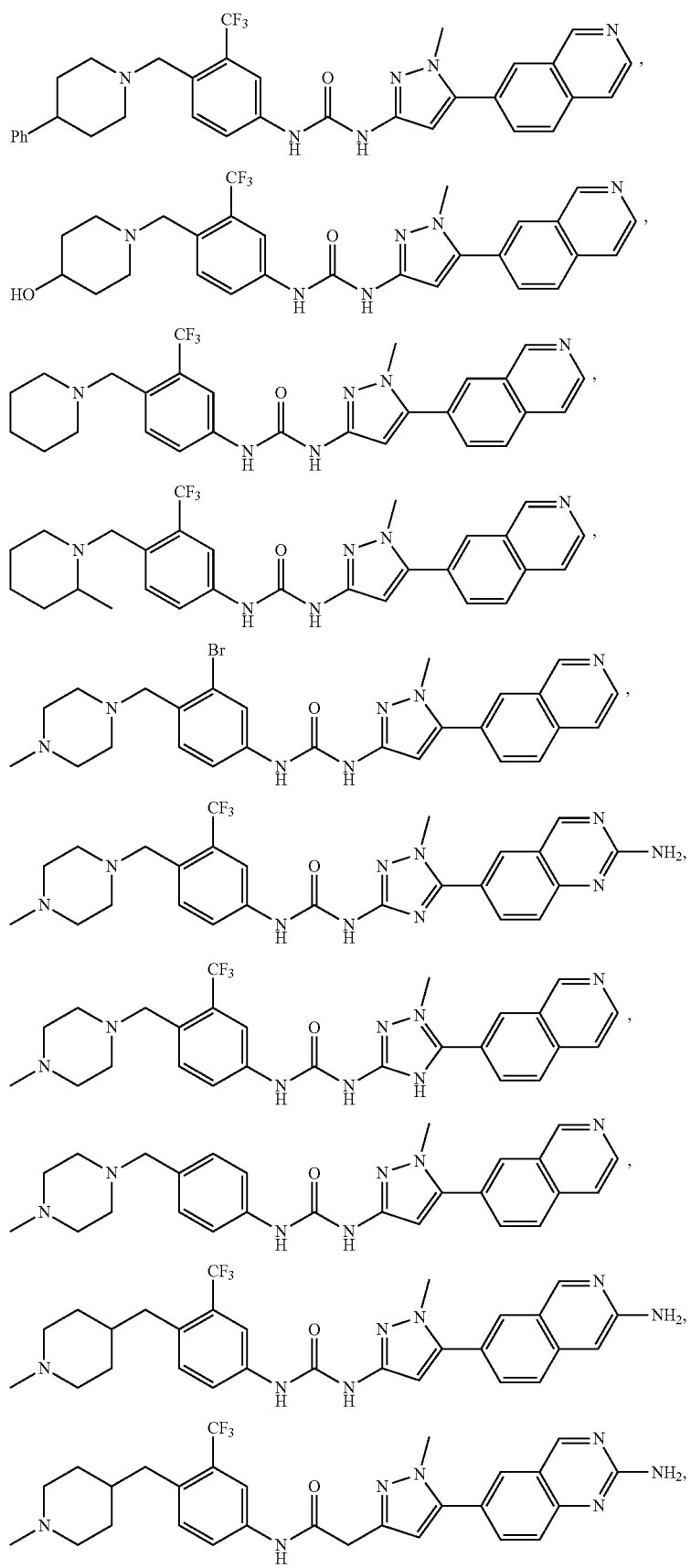

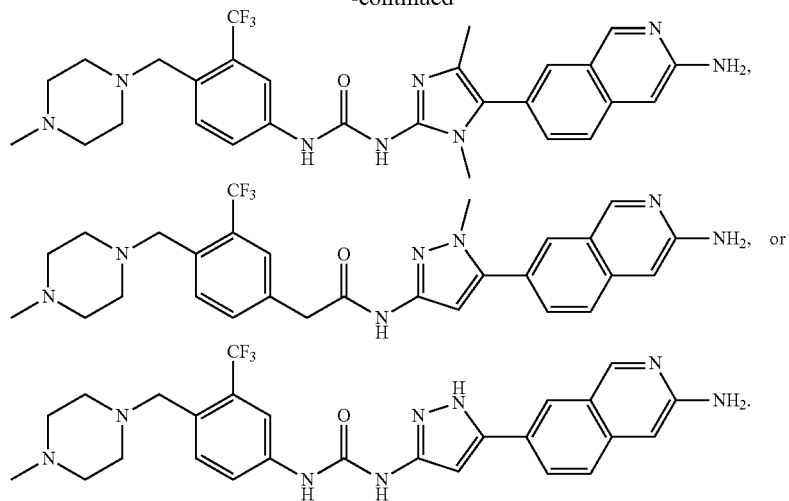
11. The compound of claim 1, wherein the compound is
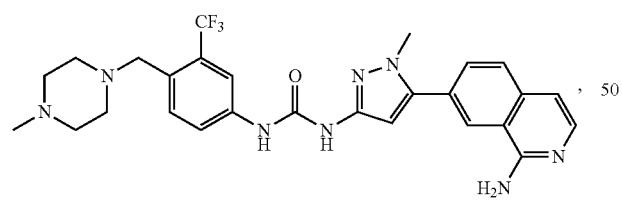
12. The compound of claim 1, wherein the compound is
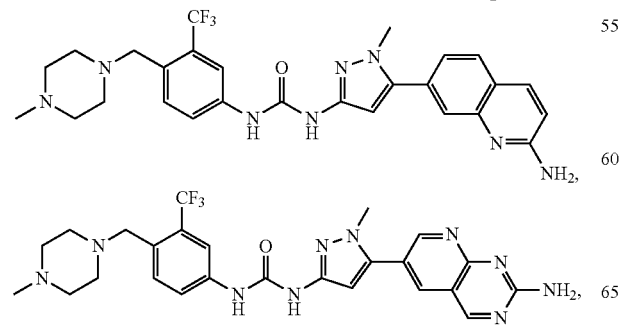
-continued
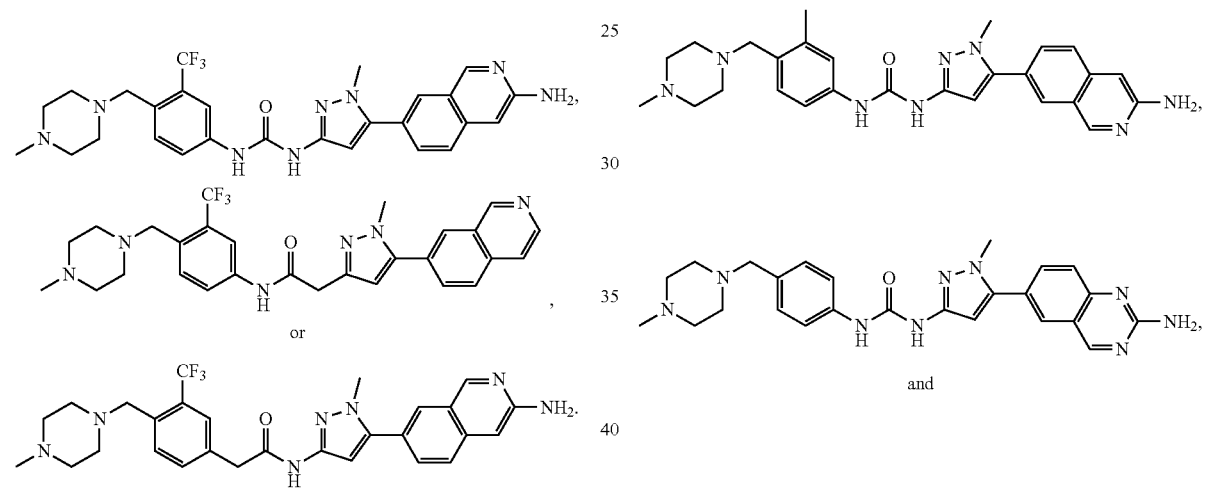
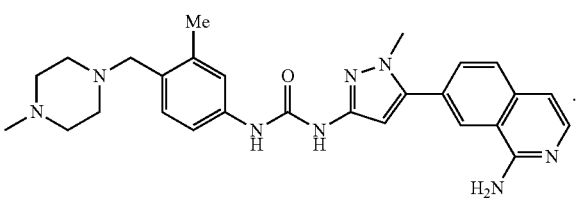
13. The compound of claim 1, wherein the compound is a compound of formula Ib:
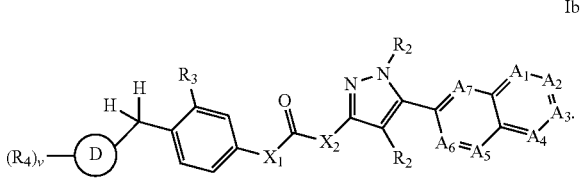
14. The compound of claim 1, wherein the compound is a compound of formula Ic:

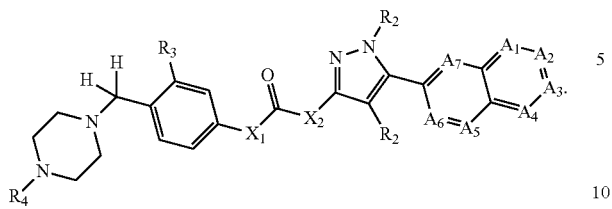
Ic
* * * * *

SEQUENCE LISTING

```
<160> NUMBER OF SEQ ID NOS: 2

<210> SEQ ID NO 1
<211> LENGTH: 17
<212> TYPE: RNA
<213> ORGANISM: Artificial Sequence
<220> FEATURE:
<223> OTHER INFORMATION: A synthetic probe

<400> SEQUENCE: 1
```

```
cauguccgca gcacaug                                                    17

<210> SEQ ID NO 2
<211> LENGTH: 17
<212> TYPE: RNA
<213> ORGANISM: Artificial Sequence
<220> FEATURE:
<223> OTHER INFORMATION: A synthetic probe

<400> SEQUENCE: 2 cauguccca gcacaug                                                     17
```